US008241670B2

(12) United States Patent
Ben-Sasson

(10) Patent No.: US 8,241,670 B2
(45) Date of Patent: Aug. 14, 2012

(54) COMPOSITIONS CAPABLE OF FACILITATING PENETRATION ACROSS A BIOLOGICAL BARRIER

(75) Inventor: Shmuel A. Ben-Sasson, Jerusalem (IL)

(73) Assignee: Chiasma Inc., Newton Centre, MA (US)

( * ) Notice: Subject to any disclaimer, the term of this patent is extended or adjusted under 35 U.S.C. 154(b) by 1071 days.

(21) Appl. No.: 11/547,568

(22) PCT Filed: Apr. 14, 2005

(86) PCT No.: PCT/IB2005/004183
§ 371 (c)(1),
(2), (4) Date: Aug. 13, 2007

(87) PCT Pub. No.: WO2006/097793
PCT Pub. Date: Sep. 21, 2006

(65) Prior Publication Data
US 2008/0159984 A1 Jul. 3, 2008

(51) Int. Cl.
*A61K 9/14* (2006.01)
*A61K 9/20* (2006.01)
*A61K 9/48* (2006.01)

(52) U.S. Cl. .................... 424/489; 424/451; 424/464
(58) Field of Classification Search .................. None
See application file for complete search history.

(56) References Cited

U.S. PATENT DOCUMENTS

| | | | |
|---|---|---|---|
| 3,869,549 A * | 3/1975 | Geller ................ 514/10.8 |
| 4,156,719 A | 5/1979 | Sezaki | |
| 4,234,437 A | 11/1980 | Friberg et al. | |
| 4,338,306 A | 7/1982 | Kitao et al. | |
| 4,485,033 A | 11/1984 | Kitao et al. | |
| 4,489,097 A | 12/1984 | Stone | |
| 4,572,915 A | 2/1986 | Crooks | |
| 4,650,665 A | 3/1987 | Kronenthal et al. | |
| 4,871,777 A | 10/1989 | Breitzke | |
| 4,895,726 A | 1/1990 | Curtet et al. | |
| 4,985,404 A * | 1/1991 | Mitchell ................ 424/489 |
| 5,200,192 A | 4/1993 | Wimmer | |
| 5,206,219 A | 4/1993 | Desai | |
| 5,246,716 A | 9/1993 | Sedun et al. | |
| 5,254,331 A | 10/1993 | Mausner | |
| 5,288,492 A | 2/1994 | Morris | |
| 5,318,781 A | 6/1994 | Shah et al. | |
| 5,443,842 A | 8/1995 | Seghizzi et al. | |
| 5,462,726 A | 10/1995 | Lodge | |
| 5,491,171 A | 2/1996 | Nishimura et al. | |
| 5,506,203 A | 4/1996 | Backstrom et al. | |
| 5,561,115 A | 10/1996 | Tenold | |
| 5,656,289 A | 8/1997 | Cho et al. | |
| 5,658,878 A | 8/1997 | Backstrom et al. | |
| 5,665,384 A | 9/1997 | Courteille et al. | |
| 5,665,711 A | 9/1997 | Sakai et al. | |
| 5,686,488 A | 11/1997 | Gamache et al. | |
| 5,714,477 A | 2/1998 | Einarsson | |
| 5,726,154 A | 3/1998 | Baudys et al. | |
| 5,738,871 A | 4/1998 | Story | |
| 5,760,096 A | 6/1998 | Thornfeldt et al. ........ 514/946 |
| 5,804,573 A | 9/1998 | Silver | |
| 5,827,534 A | 10/1998 | Fasano ................ 424/451 |
| 5,840,685 A | 11/1998 | Fujii et al. | |
| 5,853,748 A | 12/1998 | New | |
| 5,858,401 A | 1/1999 | Bhalani et al. | |
| 5,859,048 A | 1/1999 | Oohashi | |
| 5,929,030 A | 7/1999 | Hamied et al. | |
| 5,942,237 A | 8/1999 | Gizurarson et al. | |
| 6,013,657 A | 1/2000 | Lavon et al. | |
| 6,096,338 A | 8/2000 | Lacy et al. | |
| 6,114,319 A | 9/2000 | Kimura et al. | |
| 6,120,801 A | 9/2000 | Parekh et al. | |
| 6,136,336 A | 10/2000 | Tanaka et al. | |
| 6,200,602 B1 | 3/2001 | Watts et al. | |
| 6,214,380 B1 | 4/2001 | Parekh et al. | |
| 6,255,502 B1 | 7/2001 | Penkler et al. | |
| 6,322,550 B2 | 11/2001 | Iga et al. | |
| 6,326,026 B1 | 12/2001 | Parekh et al. | |
| 6,326,360 B1 | 12/2001 | Kanazawa et al. | |
| 6,333,046 B1 | 12/2001 | Sakai et al. | |
| 6,365,596 B1 | 4/2002 | Valenti | |
| 6,368,622 B2 | 4/2002 | Chen et al. | |
| 6,383,527 B1 | 5/2002 | Artman et al. | |
| 6,419,949 B1 | 7/2002 | Gasco | |
| 6,428,813 B1 | 8/2002 | Akiyama et al. | |
| 6,632,443 B2 | 10/2003 | Borowy-Borowski et al. | |
| 6,664,234 B1 * | 12/2003 | Heintz et al. ............ 514/11.3 |
| 6,696,413 B2 | 2/2004 | Fischer et al. | |

(Continued)

FOREIGN PATENT DOCUMENTS

CA 2069760 2/1998

(Continued)

OTHER PUBLICATIONS

International Search Report from corresponding international patent application No. PCT/IB2005/004183, dated Oct. 19, 2006.
Written Opinion of the International Searching Authority for corresponding international patent application PCT/IB2005/004183, dated Oct. 19, 2006.
Hsiu-I Ho et al, "Preperation of Microemulsions Using Polyglycerol Fatty Acids Esters as Surfactant for the Delivery of Protein Drugs," Journal of Pharmaceutical Sciences 85 Feb. 1996, No. 2, Washington D.C. US.
Armstrong *Physiology of the Gastrointestinal Tract*, 2$^{nd}$ Ed., Johnson, ed., Raven Press, New York, Chapter 45, 2:1251-1265 (1987).
Bernkop-Schnürch *J. Control. Release*, 52:1-16 (1998).
Citi *J. Cell Biol.*, 117(1):169-178 (1992).
Constantinides et al. *Pharm. Res.*, 11(10):1385-1390 (1994).
Delie Adv. *Drug Del. Rev.*, 34(1):221-233 (1998).
Fasano et al. *Proc. Nat. Acad. Sci. USA*, 88:5242-5246 (1991).
Filikov et al. *J. Comput. Aided Mol. Des.*, 12(3):229-240 (1998).
Fiorentini et al. *Toxicon*, 29(6):543-567 (1991).

(Continued)

*Primary Examiner* — Susan Tran
(74) *Attorney, Agent, or Firm* — Lando & Anastasi LLP

(57) ABSTRACT

This invention relates to novel penetrating compositions including one or more effectors included within a water soluble composition, immersed in a hydrophobic medium The invention also relates to methods of treating or preventing diseases by administering such penetrating compositions to affected subjects.

22 Claims, 3 Drawing Sheets

U.S. PATENT DOCUMENTS

| | | | |
|---|---|---|---|
| 6,710,195 | B2 | 3/2004 | Joshi-Hangal et al. |
| 6,720,002 | B2 | 4/2004 | Lin et al. |
| 6,770,292 | B2 * | 8/2004 | Guinez et al. ............... 424/450 |
| 6,890,961 | B2 | 5/2005 | Li et al. |
| 7,141,547 | B2 | 11/2006 | Rosen et al. |
| 7,217,431 | B2 | 5/2007 | Holm et al. |
| 7,288,520 | B2 | 10/2007 | Chang et al. |
| 7,411,039 | B2 | 8/2008 | Thim et al. |
| 2001/0055569 | A1 | 12/2001 | Davis et al. |
| 2002/0188148 | A1 | 12/2002 | O'lenick, Jr. et al. |
| 2003/0091623 | A1 | 5/2003 | Cumming et al. |
| 2003/0095928 | A1 | 5/2003 | McGurk et al. ............... 424/46 |
| 2003/0108610 | A1 | 6/2003 | Flore et al. |
| 2003/0153614 | A1 | 8/2003 | Joshi-Hangal et al. |
| 2003/0166508 | A1 | 9/2003 | Zhang |
| 2003/0176379 | A1 | 9/2003 | Raoof et al. |
| 2004/0147599 | A1 | 7/2004 | Gagnon et al. |
| 2004/0167205 | A1 | 8/2004 | Joshi-Hangal et al. |
| 2004/0248901 | A1 | 12/2004 | Lee et al. |
| 2005/0004002 | A1 | 1/2005 | Desai et al. |
| 2005/0112191 | A1 | 5/2005 | Lipari et al. |
| 2005/0142225 | A1 | 6/2005 | Kysilka et al. |
| 2005/0186277 | A1 | 8/2005 | Gale et al. |
| 2005/0209441 | A1 | 9/2005 | Lile |
| 2005/0232981 | A1 | 10/2005 | Ben-Sasson |
| 2005/0256097 | A1 | 11/2005 | Zhong et al. |
| 2005/0287203 | A1 | 12/2005 | Nijs De et al. |
| 2006/0002989 | A1 | 1/2006 | Ahmed et al. |
| 2006/0014712 | A1 | 1/2006 | Neuman |
| 2006/0052404 | A1 | 3/2006 | Rudolph et al. |
| 2006/0057185 | A1 | 3/2006 | Akimoto et al. |
| 2006/0069055 | A1 | 3/2006 | Dajee et al. |
| 2006/0078618 | A1 | 4/2006 | Constantinides |
| 2006/0128800 | A1 | 6/2006 | Penney et al. |
| 2006/0165809 | A1 | 7/2006 | Guimberteau et al. |
| 2006/0188566 | A1 * | 8/2006 | Liversidge et al. ............ 424/451 |
| 2006/0189662 | A1 | 8/2006 | Goto et al. |
| 2006/0275253 | A1 | 12/2006 | Ushida et al. |
| 2007/0004668 | A1 | 1/2007 | Raoof et al. |
| 2007/0015694 | A1 | 1/2007 | Chang et al. |
| 2007/0021325 | A1 | 1/2007 | Byun et al. |
| 2007/0104741 | A1 | 5/2007 | Murty et al. |
| 2007/0134319 | A1 | 6/2007 | Zannou et al. |
| 2007/0148228 | A1 | 6/2007 | Cumming et al. |
| 2007/0185194 | A1 | 8/2007 | Mehta et al. |
| 2007/0190139 | A1 | 8/2007 | Zerbe et al. |
| 2007/0196464 | A1 | 8/2007 | Cumming et al. |
| 2007/0207214 | A1 | 9/2007 | Castan et al. |
| 2007/0219131 | A1 | 9/2007 | Ben-Sasson et al. |
| 2007/0224142 | A1 | 9/2007 | Swaile et al. |
| 2007/0237832 | A1 | 10/2007 | Sackler et al. |
| 2007/0237833 | A1 | 10/2007 | Sackler et al. |
| 2007/0238707 | A1 | 10/2007 | Leonard |
| 2007/0248549 | A1 | 10/2007 | Kuhrts |
| 2007/0248668 | A1 | 10/2007 | Michaelis et al. |
| 2007/0254954 | A1 | 11/2007 | Sakakibara et al. |
| 2007/0259098 | A1 | 11/2007 | Gulian et al. |
| 2007/0292512 | A1 | 12/2007 | Leonard et al. |
| 2008/0275001 | A1 | 11/2008 | Cumming et al. |
| 2009/0280169 | A1 | 11/2009 | Leonard |
| 2010/0028421 | A1 | 2/2010 | Cumming et al. |
| 2010/0285143 | A1 | 11/2010 | Khedkar et al. |

FOREIGN PATENT DOCUMENTS

| | | |
|---|---|---|
| CA | 2363123 | 8/2000 |
| EP | 0366277 | 5/1990 |
| EP | 0480189 A1 | 4/1992 |
| EP | 1154761 B1 | 11/2001 |
| EP | 1424077 A1 | 6/2004 |
| WO | 97/05903 | 2/1997 |
| WO | 0050012 | 8/2000 |
| WO | WO0101960 A1 * | 1/2001 |
| WO | 03013589 A1 | 2/2003 |
| WO | 2005/094785 | 10/2005 |
| WO | 2006/097793 | 9/2006 |
| WO | 2006123360 A2 | 11/2006 |
| WO | 2010032140 A2 | 3/2010 |

OTHER PUBLICATIONS

Fox *Curr. Opin. Pharmacol.*, 2:338-344 (2002).
Gumbiner *Am. J. Physiol.*, 253:C749-C758 (1987).
Hecht et al. *J. Clin. Invest.*, 82:1516-1524 (1988).
Jackson *Physiology of the Gastrointestinal Tract*, $2^{nd}$ Ed., Johnson, ed., Raven Press, New York, Chapter 59, 2:1597-1621 (1987).
Jiao et al. *Circulation*, 105:230-235 (2002).
Madara *J. Clin. Invest.*, 83:1089-1094 (1989).
Ouyang et al. *J. Med. Chem.*, 45(13):2857-2866 (2002).
Schilfgaarde et al. *Infect. Immun.*, 68(8):4616-4623 (2000).
Wang et al. *Am. J. Respir. Cell Mol. Biol.*, 22:129-138 (2000).
Watnasirichaikul et al. *J. Pharm. Pharmacol.*, 54(4):473-480 (2002).
Yowell et al. *Cancer Treat. Rev.*, 28(Suppl. A):3-6 (2002).
Zavoico et al. *Biochimica et Biophysica Acta*, 812(2):299-312 (1985).
Charles J. Rebouche, "Carnitine Absorption: Effects of sodium valproate and sodium octanoate in the Caco-2 cell culture model of human intestinal epithelium" J. Nutr. Biochem., (Apr. 1998), vol. 9: 228-235.
Bruce J. Aungst, "Enhancement of Intestinal absorption of peptides and non-peptides" Journal of Controlled Release, (1996) vol. 41:19-31.
U.S. Appl. No. 12/553,196, filed Sep. 3, 2009.
International Search Report from corresponding international patent application No. PCT/IB 07/04569, dated Oct. 20, 2009.
European Office Action dated Dec. 16, 2011 for application No. 05 857 653.9-1219.
Hsiu-I Ho et al. "Preparation of Microemulsions Using Polyglycerol Fatty Acid Esters as Surfactant for the Delivery of Protein Drugs". Journal of Pharmaceutical Sciences, American Pharmaceutical Association. Washington, US, vol. 85 No. 2, Feb. 1, 1996, pp. 138-143.
Nir et al, "Fear of injections in young adults; prevalence and associations", Am. J. Trop. Med. Hyg., 68(3), pp. 341-344, 2003.
Wright et al., "Fear of needles—nature amd prevalence in general practice", Australian family physician, 38(3), Mar. 2003.
International Search Report dated Mar. 18, 2010 in related WO application—PCT/IB 09/07155.
International Preliminary Report on Patentability from International Application Serial No. PCT/IB07/04569 mailed Oct. 20, 2009.
Written Opinion in related WO application—PCT/IB 09/07155, dated Mar. 18, 2010.
Watnasirichaikul S. et al, "Preperation of biodegradable insulin nanocapsules from biocompatible microemulsions", PharmaceuticalResearch, vol. 17, No. 6, p. 684-689, 2000.

* cited by examiner

COMPOSITIONS CAPABLE OF FACILITATING PENETRATION ACROSS A BIOLOGICAL BARRIER

FIELD OF THE INVENTION

This invention relates to novel penetration compositions that enable efficient translocation of an effector across biological barriers.

BACKGROUND OF THE INVENTION

Techniques enabling efficient transfer of a substance of interest across a biological barrier are of considerable interest in the field of biotechnology. For example, such techniques may be used for the transport of a variety of different substances across a biological barrier regulated by tight junctions (i.e., the mucosal epithelia, which include the intestinal and respiratory epithelia and the vascular endothelia, which includes the blood-brain barrier).

The intestinal epithelium represents the major barrier to absorption of orally administered compounds, e.g., drugs and peptides, into the systemic circulation. This barrier is composed of a single layer of columnar epithelial cells (primarily enterocytes, goblet cells, endocrine cells, and paneth cells), which are joined at their apical surfaces by the tight junctions. See Madara et al., PHYSIOLOGY OF THE GASTROINTESTINAL TRACT; 2nd Ed., Johnson, ed., Raven Press, New York, pp. 1251-66 (1987).

Compounds that are presented in the intestinal lumen can enter the blood stream through active or facilitative transport, passive transcellular transport, or passive paracellular transport. Active or facilitative transport occurs via cellular carriers, and is limited to transport of low molecular weight degradation products of complex molecules such as proteins and sugars, e.g., amino acids, pentoses, and hexoses. Passive transcellular transport requires partitioning of the molecule through both the apical and basolateral membranes. This process is limited to relatively small hydrophobic compounds. See Jackson, PHYSIOLOGY OF THE GASTROINTESTINAL TRACT; 2nd Ed., Johnson, ed., Raven Press, New York, pp. 1597-1621 (1987). Consequently, with the exception of those molecules that are transported by active or facilitative mechanisms, absorption of larger, more hydrophilic molecules is, for the most part, limited to the paracellular pathway. However, the entry of molecules through the paracellular pathway is primarily restricted by the presence of the tight junctions. See Gumbiner, *Am. J. Physiol.*, 253:C749-C758 (1987); Madara, *J. Clin. Invest.*, 83:1089-94 (1989).

Considerable attention has been directed to finding ways to increase paracellular transport by "loosening" tight junctions. One approach to overcoming the restriction to paracellular transport is to co-administer, in a mixture, biologically active ingredients with absorption enhancing agents. Generally, intestinal/respiratory absorption enhancers include, but are not limited to, calcium chelators, such as citrate and ethylenediamine tetraacetic acid (EDTA); surfactants, such as sodium dodecyl sulfate, bile salts, palmitoylcarnitine, and sodium salts of fatty acids. For example, EDTA, which is known to disrupt tight junctions by chelating calcium, enhances the efficiency of gene transfer into the airway respiratory epithelium in patients with cystic fibrosis. See Wang, et al., *Am. J. Respir. Cell Mol. Biol.*, 22:129-138 (2000). However, one drawback to all of these methods is that they facilitate the indiscriminate penetration of any nearby molecule that happens to be in the gastrointestinal or airway lumen. In addition, each of these intestinal/respiratory absorption enhancers has properties that limit their general usefulness as a means to promote absorption of various molecules across a biological barrier.

Moreover, with the use of harsh surfactants, the potential lytic nature of these agents raises concerns regarding safety. Specifically, the intestinal and respiratory epithelia provide a barrier to the entry of toxins, bacteria and viruses from the hostile exterior. Hence, the possibility of exfoliation of the epithelium using surfactants, as well as the potential complications arising from increased epithelial repair, raise safety concerns about the use of surfactants as intestinal/respiratory absorption enhancers.

When calcium chelators are used as intestinal/respiratory absorption enhancers, $Ca^{+2}$ depletion does not act directly on the tight junction, but rather, induces global changes in the cells, including disruption of actin filaments, disruption of adherent junctions, diminished cell adhesion, and activation of protein kinases. See Citi, *J. Cell Biol.*, 117:169-178 (1992). Moreover, as typical calcium chelators only have access to the mucosal surface, and luminal $Ca^{+2}$ concentration may vary, sufficient amounts of chelators generally cannot be administered to lower $Ca^{+2}$ levels to induce the opening of tight junctions in a rapid, reversible, and reproducible manner.

Additionally, some toxins such as *Clostridium difficile* toxin A and B, appear to irreversibly increase paracellular permeability and are thus, associated with destruction of the tight junction complex. See Hecht, et al., *J. Clin. Invest.*, 82:1516-24 (1988); Fiorentini and Thelestam, *Toxicon*, 29:543-67 (1991). Other toxins such as *Vibrio cholerae* zonula occludens toxin (ZOT) modulate the structure of intercellular tight junctions. As a result, the intestinal mucosa becomes more permeable, yet in a non-selective manner. See Fasano, et al., *Proc. Nat. Acad. Sci., USA*, 8:5242-46 (1991); U.S. Pat. No. 5,827,534. This manipulation might also results in diarrhea.

The oral delivery of bioactive peptides and proteins has received special attention, due to their vulnerability to the harsh gastrointestinal environment, leading to enzymatic degradation and chemical denaturation. Diverse drug delivery vehicles have been employed, among them liposomes, lipidic or polymeric nanoparticles, and microemulsions. These have improved the oral bioavailability of certain drugs, mostly by the protective effect they offer. However, these vehicles do not address the impermeable nature of the epithelial barrier. Thus, for most relevant drugs, absorption does not rise above 5%, and fails to achieve the minimal therapeutic goals.

Hence, a need remains for an efficient, specific, non-invasive, low-risk means to target various biological barriers for the delivery of large bioactive molecules such as polypeptides, macromolecule drugs and other therapeutic agents.

SUMMARY OF THE INVENTION

The present invention provides compositions for effectively translocating therapeutically active molecules, i.e., effectors, otherwise impermeable through biological barriers, by including such molecules in a water soluble composition. In one embodiment, the water soluble composition can be immersed in a hydrophobic medium. Alternatively, the water soluble solution can first be lyophilized, and then suspended in a hydrophobic medium. The invention also relates to the use of membrane fluidizing agents in order to enhance the translocation of said at least one effector across a biological barrier.

"Effective translocation" or "efficient translocation" as used herein means that introduction of the composition to a biological barrier, results in at least 5%, but preferably at least 10%, and even more preferably, at least 20% translocation of the effector across the biological barrier.

As used herein, a "penetration composition" includes any composition of a water soluble composition immersed in a hydrophobic medium, that facilitates the effective translocation of a substance, e.g., at least one effector, across a biological barrier, utilizing at least one membrane fluidizing agent. The term "water soluble composition" as used herein refers to compositions which can be solubilized in a hydrophilic or partially hydrophilic solvent. A hydrophilic or partially hydrophilic solvent may consist of water, or a non-aqueous medium such as mono-alcohols, di-alcohols, or tri-alcohols. Examples of suitable mono-alcohols include, but are not limited to, ethanol, propanol, isopropanol and butanol. An example of a di-alcohol includes, but is not limited to, propylene glycol. An example of a tri-alcohol includes, but is not limited to, glycerol.

According to the methods and compositions of the invention, the water soluble composition is immersed in a hydrophobic medium. Alternatively, the water soluble solution is first lyophilized, and then suspended in a hydrophobic medium. A hydrophobic medium can consist of aliphatic, cyclic, or aromatic molecules. Examples of a suitable aliphatic hydrophobic medium include mineral oil (e.g. paraffin), fatty acids, mono-glycerides, di-glycerides, tri-glycerides, ethers, and esters. Examples of tri-glycerides include long chain triglycerides, medium chain triglycerides, and short chain triglycerides. For example, the long chain triglyceride can be castor oil, and the short chain triglyceride can be glyceryl tributyrate. Examples of a suitable cyclic hydrophobic medium include, but are not limited to, terpenoids, cholesterol, cholesterol derivatives (e.g., cholesterol sulfate), and cholesterol esters of fatty acids. An example of an aromatic hydrophobic medium includes, but is not limited to, benzyl benzoate.

The penetration composition is further supplemented by a membrane fluidizing agent. The term "membrane fluidizing agent" as used herein refers to molecules which increase the fluidity and decrease the order of lipids in biological membranes. For example, a membrane fluidizing agent can be a linear, branched, cyclical, or aromatic alcohol. Examples of suitable linear alcohols include, but are not limited to, butanol, pentanol, hexanol, heptanol, octanol, nonanol, decanol, undecanol, and dodecanol. Examples of branched alcohols include, but are not limited to, geraniol and farnesol. An example of a cyclical alcohol includes, but is not limited to, menthol. Examples of suitable aromatic alcohols include, but are not limited to, benzyl alcohol, 4-hydroxycinnamic acid, and phenolic compounds. Examples of phenolic compounds include, but are not limited to, phenol, m-cresol, and m-chlorocresol.

As used herein, the term "biological barrier" is meant to include biological membranes such as the plasma membrane as well as any biological structures sealed by tight junctions (or occluding junctions) such as the mucosal or vascular epithelia, (including, but not limited to, the gastrointestinal or respiratory epithelia), and the blood brain barrier. Moreover, those skilled in the art will recognize that translocation may occur across a biological barrier in a tissue containing cells such as epithelial cells or endothelial cells.

The invention also provides penetration compositions containing a pharmaceutically acceptable carrier or excipient, or a combination thereof. In various embodiments, the compositions of the invention can be contained within a capsule, or can take the form of a tablet, an emulsion, a cream, an ointment, a suppository or a nasal spray.

Penetration compositions include at least one effector. The at least one effector can be a therapeutically active impermeable molecule including, but not limited to, nucleic acids, glycosaminoglycans, proteins, peptides, or pharmaceutically active agents, such as, for example, hormones, growth factors, incretins, neurotrophic factors, anticoagulants, bioactive molecules, toxins, antibiotics, anti-fungal agents, antipathogenic agents, antigens, antibodies, monoclonal antibodies, antibody fragments, soluble receptors, immunomodulators, vitamins, antineoplastic agents, enzymes, gonadotropins, cytokines, or other therapeutic agents. For example, glycosaminoglycans acting as impermeable compounds include, but are not limited to, heparin, heparin derivative, heparan sulfate, chondroitin sulfate, dermatan sulfate, and hyaluronic acid. Examples of heparin derivatives include, but are not limited to, low molecular weight heparins such as enoxaparin, dalteparin, tinzaparin, and fondaparinux. Nucleic acids serving as impermeable molecules include, but are not limited to, specific DNA sequences (e.g., coding genes), specific RNA sequences (e.g., RNA aptamers, antisense RNA or a specific inhibitory RNA (RNAi)), poly CpG, or poly I:C synthetic polymers of nucleic acids. Other suitable proteins include, but are not limited to, insulin, erythropoietin (EPO), glucagon-like peptide 1 (GLP-1), melanocyte stimulating hormone ($\alpha$MSH), parathyroid hormone (PTH), parathyroid hormone amino acids 1-34 (PTH(1-34)), growth hormone, peptide YY amino acids 3-36 (PYY(3-36)), calcitonin, interleukin-2 (IL-2), $\alpha$1-antitrypsin, granulocyte/monocyte colony stimulating factor (GM-CSF), granulocyte colony stimulating factor (G-CSF), T20, anti-TNF antibodies, interferon $\alpha$, interferon $\beta$, interferon $\gamma$, luteinizing hormone (LH), follicle-stimulating hormone (FSH), enkephalin, dalargin, kyotorphin, basic fibroblast growth factor (bFGF), hirudin, hirulog, luteinizing hormone releasing hormone (LHRH) analog, brain-derived natriuretic peptide (BNP), glatiramer acetate, and neurotrophic factors.

Suitable effectors also include pharmaceutically active agents selected from the group consisting of vitamin B12, a bisphosphonate, taxol, Caspofungin, or an aminoglycoside antibiotic.

As used herein, "impermeable molecules" are molecules that are unable to efficiently cross biological barriers, such as the cell membrane or tight junctions. Typically, impermeable molecules of the invention are of a molecular weight above 200 Daltons. Anionic impermeable molecules are preferably polysaccharides, i.e., glycosaminoglycans, nucleic acids, or net negatively charged proteins, whereas cationic impermeable molecules are preferably net positively charged proteins.

A protein's net charge is determined by two factors: 1) the total count of acidic amino acids vs. basic amino acids, and 2) the specific solvent pH surroundings, which expose positive or negative residues. As used herein, "net positively or net negatively charged proteins" are proteins that, under non-denaturing pH surroundings, have a net positive or net negative electric charge. For example, interferon $\beta$ is a protein that contains 23 positively charged residues (lysines and arginines), and 18 negatively charged residues (glutamic or aspartic acid residues). Therefore, under neutral or acidic pH surroundings, interferon $\beta$ constitutes a net positively charged protein. Conversely, insulin is a 51 amino acid protein that contains two positively charged residues, one lysine and one arginine, and four negatively charged glutamic acid residues. Therefore, under neutral or basic pH surroundings, insulin constitutes a net negatively charged protein. In general, those skilled in the art will recognize that all proteins may be considered "net negatively charged proteins" or "net positively charged proteins", regardless of their amino acid composition, depending on their pH and/or solvent surroundings. For example, different solvents can expose negative or positive side chains depending on the solvent pH.

The water soluble compositions of this invention may further contain a stabilizer of protein structure. "Stabilizers of protein structure", as used herein, refer to any compounds that can stabilize protein structure under aqueous or non-aqueous conditions, such as polycationic molecules, polyanionic molecules, and uncharged polymers. One example of a polycationic molecule that can function as a protein stabilizer is a polyamine such as spermine. Examples of polyanionic molecule that can function as protein stabilizers include, but are not limited to, phytic acid and sucrose octasulfate. Non-limiting examples of uncharged polymers that can function as protein stabilizers include polyvinylpyrrolidone and polyvinyl alcohol.

The water soluble compositions of this invention may further contain amphipathic counter ions. Counter ions can include, for example, anionic or cationic amphipathic molecules. In one embodiment, anionic or cationic counter ions of this invention are ions that are negatively (anionic) or positively (cationic) charged and can include a hydrophobic moiety. Under appropriate conditions, anionic or cationic counter ions can establish electrostatic interactions with cationic or anionic impermeable molecules, respectively. The formation of such a complex can cause charge neutralization, thereby creating a new uncharged entity, with further hydrophobic properties in the case of an inherent hydrophobicity of the counter ion.

Contemplated cationic counter ions include quaternary amine derivatives, such as benzalkonium derivatives. Suitable quaternary amines can be substituted by hydrophobic residues. In general, quaternary amines contemplated by the invention have the structure: 1-R1-2-R2-3-R3-4-R4-N, wherein R1, 2, 3, or 4 are alkyl or aryl derivatives. Further, quaternary amines can be ionic liquid forming cations, such as imidazolium derivatives, pyridinium derivatives, phosphonium compounds or tetraalkylammonium compounds. For example, imidazolium derivatives have the general structure of 1-R1-3-R2-imidazolium where R1 and R2 can be linear or branched alkyls with 1 to 12 carbons. Such imidazolium derivatives can be further substituted for example by halogens or an alkyl group. Specific imidazolium derivatives include, but are not limited to, 1-ethyl-3-methylimidazolium, 1-butyl-3-methylimidazolium, 1-hexyl-3-methylimidazolium, 1-methyl-3-octylimidazolium, 1-methyl-3-(3,3,4,4,5,5,6,6,7,7,8,8,8-tridecafluorooctyl)-imidazolium, 1,3-dimethylimidazolium, and 1,2-dimethyl-3-propyl imidazolium.

Pyridinium derivatives have the general structure of 1-R1-3-R2-pyridinium where R1 is a linear or branched alkyl with 1 to 12 carbons, and R2 is H or a linear or branched alkyl with 1 to 12 carbons. Such pyridinium derivatives can be further substituted for example by halogens or an alkyl group. Pyridinium derivatives include, but are not limited to, 3-methyl-1-propylpyridinium, 1-butyl-3-methylpyridinium, and 1-butyl-4-methylpyridinium. The ionic liquid forming cations described herein can also be constituents of water soluble salts.

Suitable anionic counter ions are ions with negatively charged residues such as carboxylate, sulfonate or phosphonate anions, and can further contain a hydrophobic moiety. Examples of such anionic counter ions include, but are not limited to, sodium dodecyl sulphate, dioctyl sulfosuccinate and other anionic compounds derived from organic acids.

The penetration compositions of this invention may also contain a surface active agent. Suitable surface active agents include ionic and non-ionic detergents. Ionic detergents can be fatty acid salts, lecithin, or bile salts. Examples of fatty acid salts include, but are not limited to, sodium octanoate, sodium decanoate, and sodium dodecanoate. Non-limiting examples of non-ionic detergents include cremophore, a polyethylene glycol fatty alcohol ether, a sorbitan fatty acid ester, Solutol HS15, or a poloxamer. Examples of sorbitan fatty acid esters include, but are not limited to, sorbitan monolaurate, sorbitan monooleate, and sorbitan monopalmitate.

The penetration compositions of this invention may also contain adhesive polymers such as methylcellulose, ethylcellulose, hydroxypropylmethylcellulose (HPMC), or carbopol. Additionally, the penetration compositions of this invention may also contain a monoglyceride. Examples of monoglycerides include, but are not limited to, glyceryl monooctanoate, glyceryl monodecanoate, glyceryl monolaurate, glyceryl monomyristate, glyceryl monostearate, glyceryl monopalmitate, and glyceryl monooleate.

In one embodiment, the penetration compositions of this invention contain at least one effector, with spermine, polyvinylpyrrolidone, and sodium dodecanoate immersed with octanol and geraniol in a vegetarian oil such as castor oil, or in a combination of medium chain triglycerides, or glyceryl tributyrate and castor oil. The composition can further contain sorbitan monopalmitate and/or glyceryl monooleate and/or methylcellulose and/or cholesterol sulfate.

The penetration compositions of this invention can further contain a protective agent. An example of a protective agent is a protease inhibitor. Suitable protease inhibitors that can be added to the penetration composition are described in Bernkop-Schnurch et al., *J. Control. Release*, 52:1-16 (1998). These include, for example, inhibitors of luminally secreted proteases, such as aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly(acrylate) derivatives, chymostatin, benzyloxycarbonyl-Pro-Phe-CHO, FK-448, sugar biphenylboronic acids complexes, β-phenylpropionate, elastatinal, methoxysuccinyl-Ala-Ala-Pro-Val-chloromethylketone (MPCMK), EDTA, and chitosan-EDTA conjugates. Suitable protease inhibitors also include inhibitors of membrane bound proteases, such as amino acids, di- and tripeptides, amastatin, bestatin, puromycin, bacitracin, phosphinic acid dipeptide analogues, α-aminoboronic acid derivatives, Na-glycocholate, 1,10-phenanthroline, acivicin, L-serine-borate, thiorphan, and phosphoramidon.

Preferred compositions include, e.g., enteric-coated tablets and gelatin or hydroxypropyl methylcellulose (HPMC) capsules comprising the active ingredient together with a) diluents, e.g., lactose, dextrose, sucrose, mannitol, sorbitol, cellulose and/or glycine; b) protease inhibitors such as Aprotinin or trasylol; c) lubricants, e.g., silica, talcum, stearic acid, its magnesium or calcium salt, poloxamer and/or polyethyleneglycol; for tablets also d) binders, e.g., magnesium aluminum silicate, starch paste, gelatin, tragacanth, methylcellulose, sodium carboxymethylcellulose and/or polyvinylpyrrolidone; e) ionic surface active agents such as poloxamer, Solutol HS15, Cremophore, phospholipids and bile acids, if desired f) disintegrants, e.g., starches, agar, alginic acid or its sodium salt, or effervescent mixtures; and/or g) absorbents, colorants, flavors and sweeteners. Suppositories are advantageously prepared from fatty emulsions or suspensions. The compositions may be sterilized and/or contain adjuvants, such as preserving, reducing agents e.g., NAC(N-Acetyl-L-Cysteine), stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, and contain about 0.001 to 75%, and preferably about 0.01 to 10%, of the active ingredient.

The compositions may further contain a mixture of at least two substances selected from the group consisting of a non-ionic detergent, an ionic detergent, an adhesive polymer, a monoglyceride, a protease inhibitor, a sulfohydryl group status modifying agent, and an antioxidant. For example, the non-ionic detergent may be a poloxamer, cremophore, a polyethylene glycol fatty alcohol ether, a sorbitan fatty acid ester or Solutol HS15; the ionic detergent may be a fatty acid salt; the adhesive polymer may be methylcellulose, ethylcellulose, hydroxypropylmethylcellulose (HPMC), or carbopol; the monoglyceride may be glyceryl monooctanoate, glyceryl monodecanoate, glyceryl monolaurate, glyceryl monomyristate, glyceryl monostearate, glyceryl monopalmitate, or glyceryl monooleate; the protease inhibitor may be selected from the group consisting of aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly (acrylate) derivatives, chymostatin, benzyloxycarbonyl-Pro-Phe-CHO, FK-448, sugar biphenylboronic acids complexes, β-phenylpropionate, elastatinal, methoxysuccinyl-Ala-Ala-Pro-Val-chloromethylketone (MPCMK), EDTA, chitosan-EDTA conjugates, amino acids, di-peptides, tripeptides, amastatin, bestatin, puromycin, bacitracin, phosphinic acid dipeptide analogues, α-aminoboronic acid derivatives, Na-glycocholate, 1,10-phenanthroline, acivicin, L-serine-borate, thiorphan, and phosphoramidon; the sulfohydryl group status modifying agent may be N-acetyl L-cysteine (NAC) or Diamide; and/or the antioxidant may be selected from the group consisting of tocopherol, deteroxime mesylate, methyl paraben, ethyl paraben, and ascorbic acid.

The invention also provides kits having one or more containers containing a therapeutically or prophylactically effective amount of a composition of the invention.

Methods for making and using the present pharmaceutical compositions are also within the scope of the present invention.

The invention also involves methods of effectively translocating at least one effector across a biological barrier using the compositions of the invention. For example, at least one effector can be included within a water soluble composition, optionally lyophilized thereafter, immersed in a hydrophobic medium to form a composition according to the invention, which can then be introduced to a biological barrier, thereby effectively translocating the effector across the biological barrier.

Also described are methods of treating or preventing diseases or pathological conditions by administering to a subject in which such treatment or prevention is desired, a composition of the invention in an amount sufficient to treat or prevent the disease or pathological condition. For example, the diseases or conditions to be treated include, but are not limited to, endocrine disorders, including diabetes, infertility, hormone deficiencies and osteoporosis; opthalmological disorders; neurodegenerative disorders, including Alzheimer's disease and other forms of dementia, Parkinson's disease, multiple sclerosis, and Huntington's disease; cardiovascular disorders, including atherosclerosis, hyper- and hypocoagulable states, coronary disease, and cerebrovascular events; metabolic disorders, including obesity and vitamin deficiencies; renal disorders, including renal failure; haematological disorders, including anemia of different entities; immunologic and rheumatologic disorders, including autoimmune diseases, and immune deficiencies; infectious diseases, including viral, bacterial, fungal and parasitic infections; neoplastic diseases; and multi-factorial disorders, including impotence, chronic pain, depression, different fibrosis states, and short stature.

Administration of the active compounds and salts described herein can be via any of the accepted modes of administration for therapeutic agents. These methods include oral, buccal, anal, rectal, bronchial, pulmonary, nasal, sublingual, intraorbital, parenteral, transdermal, or topical administration modes.

Also included in the invention are methods of producing the compositions described herein. For example, the water soluble composition containing the effector can be dissolved or suspended in a hydrophilic or partially hydrophilic solvent that is further immersed together with a membrane fluidizing agent in a hydrophobic medium, thereby producing the composition. Alternatively, the water soluble composition including the effector, or any combination of effector, protein stabilizers, and/or counter ions can be lyophilized together and then suspended with a membrane fluidizing agent in a hydrophobic medium. In general, the entire water soluble composition can be first lyophilized and then suspended in a hydrophobic medium. Other components of the composition can also be optionally lyophilized or added during reconstitution of the lyophilized materials.

Also provided are methods of mucosal, i.e., oral, nasal, rectal, vaginal, or bronchial, vaccination involving administering to a subject in need of vaccination an effective amount of a composition of the invention, wherein the effector includes an antigen to which vaccination is desired. In one embodiment, the effector can be a protective antigen (PA) for use in a vaccine against Anthrax. In another embodiment, the effector can be a Hepatitis B surface antigen (HBs) for use in a vaccine against Hepatitis B.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

Figure 1:
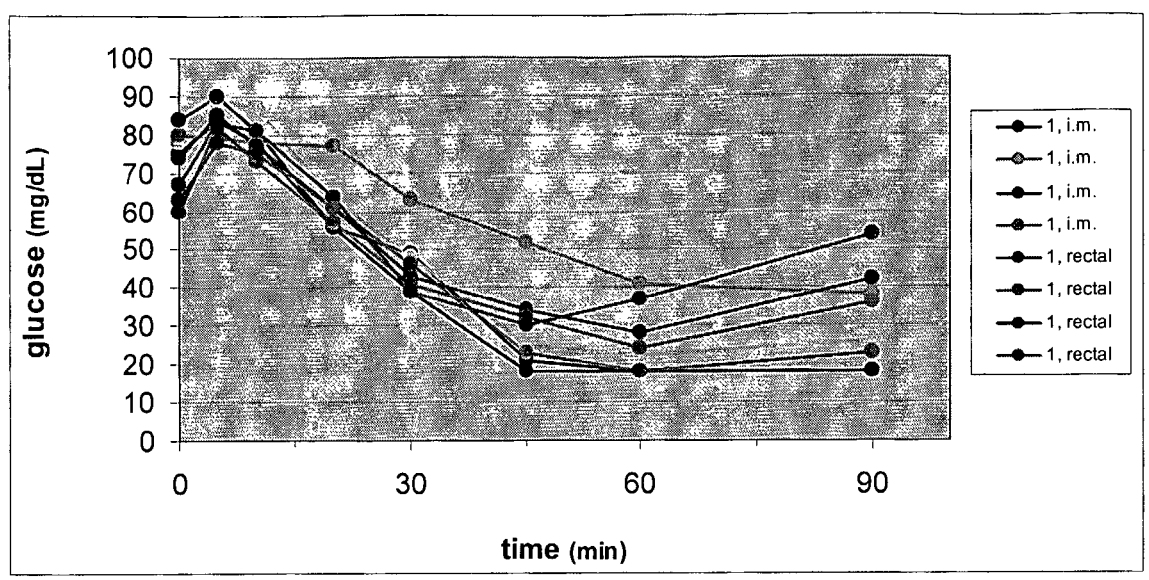
FIG. 1 depicts the gradual and significant drop in blood glucose levels as a result of using the penetration composition of the invention to translocate insulin across the intestine in rats. Preparations were administered either i.m. or rectally, and blood glucose levels were measured at various time intervals thereafter.

The present invention provides compositions for penetration that specifically target various tissues, especially those containing epithelial and endothelial cells, for the delivery of drugs and other therapeutic agents across a biological barrier. Existing transport systems known in the art are too limited to be of general application, because they are inefficient, they alter the biological properties of the active substance, they compromise the target cell, they irreversibly destroy the biological barrier and/or they invention, the composition contains an impermeable effector in a water soluble composition together with a membrane fluidizing agent. This complex can be optionally lyophilized and then immersed in a hydrophobic medium. The immersion of the water soluble composition containing the at least one effector, or a lyophilizate thereof, in the hydrophobic medium results in an intimate and unique association between the effector and the penetration enhancing compounds, thereby enabling the once impermeable effector to efficiently translocate across a biological barrier. The compositions of the present invention can be defined by their efficiency, as they must enable translocation of at least 5% (but preferably 10% or even 20%) of the at least one effector across an epithelial barrier. This efficiency is greater than that of other compositions known in the art, which typically enable translocation of only about 1-3% of the effector.

The compositions of the instant invention selectively allow the translocation of the effector across the biological barrier. The hydrophobic medium serves as a shield, thereby preventing neighboring molecules, such as proteins, toxins, or other "bystander" molecules, from co-translocating through the biological barrier with the at least one effector.

In recent years, many new drugs, peptide and protein therapeutics among them, have been developed and approved. Many others are in advanced stages of clinical testing. However, the development of satisfactory delivery systems for these rapidly evolving therapeutic agents has not kept pace. These novel drugs have very low gastrointestinal absorption rates and many of them have short in vivo half-lives, which often necessitate their delivery by infusions or frequent injections.

Some success has been achieved with the use of nano- and microparticles to enhance oral bioavailability of poorly absorbed drugs or to induce mucosal immune response. See review by Delie in *Adv. Drug Del. Rev.,* 34:221-233 (1998). Nanoparticles can be made as colloidal polymeric drug carriers that hold promise for peroral drug delivery. These polymeric dosage forms offer the advantages of a sustained and continuous delivery to tissues, encapsulation and protection against degradative enzymes, and enhance site-specific delivery. Macromolecules, such as hormones, have been entrapped within polymeric particles. See Jiao et al., *Circulation,* 105: 230-235 (2002), for an evaluation of oral heparin-loaded polymeric nanoparticles.

In the development of new oral dosage forms, particular emphasis has been placed on the development of lipid-based systems. Much of the focus has been on the development of microemulsions as drug solubilization and absorption enhancement systems. See review by Constantinides et al., in *Pharm. Res.,* 11(10):1385-1390 (1994).

Commonly used microemulsions are thermodynamically stable dispersions of one liquid phase into another, that involve a combination of at least three components—oil, water, and a surfactant. Both water-in-oil (w/o) and oil-in-water (o/w) microemulsions have been proposed to enhance the oral bioavailability of drugs. They offer improved drug solubilization and protection against enzymatic hydrolysis, as well as the potential for enhanced absorption afforded by surfactant-induced membrane permeability changes. For example, the oral release and bioactivity of insulin in water-in-oil microemulsions is described by Watnasirichaikul et al., in *J. Pharm. Pharm.,* 54:473-480 (2002).

As described above, the penetration compositions of this invention contains at least one effector in a water soluble composition immersed in a hydrophobic medium, which facilitates the effective translocation of the at least one effector across a biological barrier. Unlike emulsions, where water is an essential constituent of the formulation, the water soluble composition, according to the present invention, can be dissolved either in water or in a non-aqueous medium such as, for example, mono-alcohols, di-alcohols, or tri-alcohols. Moreover, the water soluble composition according to the present invention can be totally evaporated, via lyophilization, prior to suspension in the hydrophobic medium.

Additionally, unlike the water-in-oil (w/o) and oil-in-water (o/w) microemulsions, where the use of a surfactant is obligatory, the penetration compositions of this invention offers an oral delivery system whereby the addition of a surface active agent is optional.

Suitable hydrophobic mediums can contain, for example, aliphatic, cyclic, or aromatic molecules. Examples of a suitable aliphatic hydrophobic medium include, but are not limited to, mineral oil (e.g., paraffin), fatty acids, mono-glycerides, di-glycerides, tri-glycerides, ethers, and esters. Examples of tri-glycerides include, but are not limited to, long chain triglycerides, medium chain triglycerides, and short chain triglycerides. For example, the long chain triglyceride can be castor oil, and the short chain triglyceride can be glyceryl tributyrate. Examples of a suitable cyclic hydrophobic medium include, but are not limited to, terpenoids, cholesterol, cholesterol derivatives (e.g., cholesterol sulfate), and cholesterol esters of fatty acids. A non-limiting example of an aromatic hydrophobic medium includes benzyl benzoate.

One example of a penetration composition contemplated by the instant invention includes insulin dissolved in water, which is then lyophilized and immersed in castor oil, or a combination of castor oil and medium chain triglycerides ("MCT") or glyceryl tributyrate. Membrane fluidizing agents, such as octanol and geraniol, for example, can also be included within the hydrophobic medium to further facilitate translocation of the effector.

In a further embodiment, the compositions of this invention employ membrane fluidizing agents. For example, a membrane fluidizing agent may be a linear, branched, cyclical, or aromatic alcohol. Examples of suitable linear alcohols include, but are not limited to, butanol, pentanol, hexanol, heptanol, octanol, nonanol, decanol, undecanol, and dodecanol. Non-limiting examples of branched alcohols include geraniol and farnesol. An example of a cyclical alcohol includes menthol. Examples of suitable aromatic alcohols can include benzyl alcohol, 4-hydroxycinnamic acid, and phenolic compounds. Examples of phenolic compounds can include phenol, m-cresol, and m-chlorocresol.

As described above, membrane fluidizing agents increase the fluidity and decrease the order of lipids in biological membranes. This alteration of membrane dynamics may be detected by the decrease in the steady state anisotropy of fluorescent membrane probes, such as 1,6-diphenyl-1,3,5-hexatriene. Normal alcohols, or n-alkanols, are known membrane fluidizing agents. Due to their amphipathic properties, they partition the membrane lipid bilayer with their hydroxyl moiety near the phospholipids polar headgroups, and their aliphatic chains intercalated among the fatty acyl chains of the phospholipids. Alkanols of increasing chain length penetrate the bilayer to increasing depths, and thus affect bilayer order and dynamics to a different extent. See Zavoico et al., *Biochim. Biophys Acta,* 812:299-312 (1985).

Notably, the literature teaches away from using membrane fluidizing agents to enhance paracellular transport, as no correlation is seen between induction of membrane fluidity and the ability to enhance the paracellular route. See Ouyang et al., *J. Med. Chem.,* 45:2857-2866 (2002).

In another embodiment, the compositions of this invention further contain a stabilizer of protein structure. As described above, stabilizers of protein structure are compounds that stabilize protein structure under aqueous or non-aqueous conditions. Stabilizers of protein structure can be polyanionic molecules, such as phytic acid and sucrose octasulfate, or polycationic molecules, such as spermine. Uncharged polymers, such as polyniylpyrrolidone and polyvinyl alcohol, are also suitable stabilizers.

Phytic acid and its derivatives are biologically active compounds known to bind several proteins with high affinity. Phytic acid contains six phosphate residues attached to a cyclohexane ring, enabling it to bind several guanidinium groups of arginines. See for example Filikov et al., *J. Comput. Aided Mol. Des.* 12:229-240 (1998).

As described herein, amphipathic cationic or anionic counter ions of the invention can be utilized for enabling or facilitating effective translocation of at least one effector across biological barriers. Cationic counter ions of this invention are ions that are positively charged and in addition may include a hydrophobic moiety. Anionic counter ions of this invention are ions that are negatively charged and in addition may include a hydrophobic moiety. Under appropriate conditions, cationic or anionic counter ions can establish electrostatic interactions with anionic or cationic impermeable molecules, respectively. The formation of such a complex can cause charge neutralization, thereby creating a new uncharged entity, with further hydrophobic properties in case of an inherent hydrophobicity of the counter ion.

The use of the penetration compositions described herein allows for high reproducibility, extensive and simple application for a wide variety of therapeutic molecules, and allows for the potential for highly efficient delivery through biological barriers in an organism. Accordingly, these compositions have the potential to improve upon conventional transporters such as liposomes or viruses for the efficient delivery of many macromolecules, including nucleic acids. The methods of the present invention employ the use of an effector included in a water soluble composition, which is optionally lyophilized and subsequently immersed in a hydrophobic medium, to create penetration compositions that effectively transport macromolecules across biological barriers.

The compositions of the present invention exhibit effective, non-invasive delivery of an unaltered biologically active substance (i.e., an effector) and thus, have many uses. For example, the compositions of the invention can be used in the treatment of diabetes. Insulin levels in the blood stream must be tightly regulated. The compositions of the invention can be used to deliver insulin, for example, across the mucosal epithelia, at a high yield. Other non-invasive insulin delivery methods, previously known in the art, have typical yields of 1-4% and cause intolerable fluctuations in the amount of insulin absorbed. Another treatment for elevated blood glucose levels involves the use of glucagon-like peptide 1 (GLP-1). GLP-1 is a potent hormone, which is endogenously secreted in the gastrointestinal tract upon food injection. GLP-1's important physiological action is to augment the secretion of insulin in a glucose-dependant manner, thus allowing for treatment of diabetic states.

In addition, these compositions also can be used to treat conditions resulting from atherosclerosis and the formation of thrombi and emboli such as myocardial infarction and cerebrovascular accidents. Specifically, the compositions can be used to deliver heparin or low molecular weight heparin across the mucosal epithelia. Heparin is an established effective and safe anticoagulant. However, its therapeutic use is limited by the need for parenteral administration. Thus far, there has been limited success in the direction of increasing heparin absorption from the intestine, and a sustained systemic anticoagulant effect has not been achieved.

The compositions of this invention can also be used to treat hematological diseases and deficiency states that are amenable to administration of hematological growth factors. For example, erythropoietin is a glycoprotein that stimulates red blood cell production. It is produced in the kidney and stimulates the division and differentiation of committed erythroid progenitors in the bone marrow. Endogenously, hypoxia and anemia generally increase the production of erythropoietin, which in turn stimulates erythropoiesis. However, in patients with chronic renal failure (CRF), production of erythropoietin is impaired. This erythropoietin deficiency is the primary cause of their anemia. Recombinant EPO stimulates erythropoiesis in anemic patients with CRF, including patients on dialysis, as well as those who do not require regular dialysis. Additional anemia states treated by EPO include Zidovudine-treated HIV-infected patients, and cancer patients on chemotherapy. Anemia observed in cancer patients may be related to the disease itself or the effect of concomitantly administered chemotherapeutic agents.

Another widespread cause of anemia is pernicious anemia, which is caused by a lack of vitamin B12. The complex mechanism of vitamin B12 absorption in the gastrointestinal tract involves the secretion and binding to Intrinsic Factor. This process is abnormal in pernicious anemia patients, resulting in lack of vitamin B12 absorption and anemia. The penetration compositions of the invention can be used to deliver vitamin B12 across the mucosal epithelia at high yield.

Colony stimulating factors are glycoproteins which act on hematopoietic cells by binding to specific cell surface receptors and stimulating proliferation, differentiation, commitment, and some end-cell functional activation. Granulocyte-colony stimulation factor (G-CSF) regulates the production of neutrophils within the bone marrow and affects neutrophil progenitor proliferation, differentiation and selected end-cell functional activation, including enhanced phagocytic ability, priming of the cellular metabolism associated with respiratory burst, antibody dependent killing, and the increased expression of some functions associated with cell surface antigens. In cancer patients, recombinant granulocyte-colony stimulating factor has been shown to be safe and effective in accelerating the recovery of neutrophil counts following a variety of chemotherapy regimens, thus preventing hazardous infectious. G-CSF can also shorten bone marrow recovery when administered after bone marrow transplantations.

The compositions of this invention can also be used to administer monoclonal antibodies for different indications. For example, administration of antibodies that block the signal of tumor necrosis factor (TNF) can be used to treat pathologic inflammatory processes such as rheumatoid arthritis (RA), polyarticular-course juvenile rheumatoid arthritis (JRA), as well as the resulting joint pathology.

Additionally, the compositions of this invention can be used to treat osteoporosis. It has recently been shown that intermittent exposure to parathyroid hormone (PTH), as occurs in recombinant PTH injections, results in an anabolic response, rather than the well known catabolic reaction induced by sustained exposure to elevated PTH levels, as seen in hyperparathyroidism. Thus, non invasive administration of PTH may be beneficial for increasing bone mass in various deficiency states, including osteoporosis. See Fox, *Curr. Opin. Pharmacol.*, 2:338-344 (2002).

Currently, the delivery of effectors (e.g., the delivery of insulin, erythropoietin, or heparin to the blood stream) requires invasive techniques such as intravenous or intramuscular injections. One advantage of the compositions of this invention is that they can deliver such effectors across biological barriers through non-invasive administration, including, for example oral, buccal, nasal, rectal, inhalation, insufflation, transdermal, or depository. In addition, a further advantage of the compositions of the invention is that they might be able to cross the blood-brain barrier, thereby delivering effectors to the central nervous system (CNS).

Compositions of this invention facilitate the effective passage, translocation, or penetration of a substance (e.g., an effector) across a biological barrier, particularly through or between cells sealed by tight junctions. Translocation may be detected and quantified by any method known to those skilled in the art, including using imaging compounds such as radioactive tagging and/or fluorescent probes or dyes incorporated into a hydrophobic composition in conjunction with a paracytosis assay as described in, for example, Schilfgaarde, et al., *Infect. and Immun.*, 68(8):4616-23 (2000). Generally, a paracytosis assay is performed by: a) incubating a cell layer with a composition described by this invention; b) making cross sections of the cell layers; and c) detecting the presence of the effectors, or any other component of the compositions of this invention. The detection step may be carried out by incubating the fixed cell sections with labeled antibodies directed to a component of the compositions of this invention, followed by detection of an immunological reaction between the component and the labeled antibody. Alternatively, a component of the compositions may be labeled using a radioactive label, or a fluorescent label, or a dye in order to directly visualize the paracellular location of the component. Further, a bioassay can be used to monitor the compositions' translocation. For example, using a bioactive molecule such as insulin, included in a composition, the drop in blood glucose level can be measured.

"Effective translocation" or "efficient tranlsocation" as used herein means that introduction of the composition to a biological barrier results in at least 5%, but preferably at least 10%, and even more preferably at least 20%, translocation of the effector across the biological barrier.

As used herein, the term "effector" refers to any impermeable molecule or compound serving as, for example, a biological, therapeutic, pharmaceutical, or diagnostic agent. An anionic impermeable molecule can consist of nucleic acids (ribonucleic acid, deoxyribonucleic acid) from various origins, and particularly from human, viral, animal, eukaryotic or prokaryotic, plant, or synthetic origin, etc. A nucleic acid of interest may be of a variety of sizes, ranging from, for example, a simple trace nucleotide to a genome fragment, or an entire genome. It may be a viral genome or a plasmid.

Alternatively, the effector of interest can also be a protein, such as, for example, an enzyme, a hormone, an incretin, a glycosaminoglycan, a cytokine, an apolipoprotein, a growth factor, a bioactive molecule, an antigen, or an antibody, etc. Glycosaminoglycans include, but are not limited to, heparin, heparin derivatives, heparan sulfate, chondroitin sulfate, dermatan sulfate, and hyaluronic acid. Examples of heparin derivatives include, but are not limited to, low molecular weight heparins such as enoxaparin, dalteparin, tinzaparin, and fondaparinux. As used herein, the term "bioactive molecule" refers to those compounds that have an effect on or elicit a response from living cells, tissues, or the organism as a whole. A non-limiting example of a bioactive molecule is a protein. Other examples of the bioactive molecule include, but are not limited to insulin, erythropoietin (EPO), glucagon-like peptide 1 (GLP-1), melanocyte stimulating hormone ($\alpha$MSH), parathyroid hormone (PTH), parathyroid hormone amino acids 1-34 (PTH(1-34)), growth hormone, peptide YY amino acids 3-36 (PYY(3-36)), calcitonin, interleukin-2 (IL-2), $\alpha$-antitrypsin, granulocyte/monocyte colony stimulating factor (GM-CSF), granulocyte colony stimulating factor (G-CSF), T20, anti-TNF antibodies, interferon $\alpha$, interferon $\beta$, interferon $\gamma$, luteinizing hormone (LH), follicle-stimulating hormone (FSH), enkephalin, dalargin, kyotorphin, basic fibroblast growth factor (bFGF), hirudin, hirulog, luteinizing hormone releasing hormone (LHRH) analog, brain-derived natriuretic peptide (BNP), glatiramer acetate, and neurotrophic factors.

Furthermore, the effector can be a pharmaceutically active agent, such as, for example, a toxin, a therapeutic agent, or an antipathogenic agent, such as an antibiotic, an antiviral, an antifungal, or an anti-parasitic agent. The effector of interest can itself be directly active or can be activated in situ by the composition, by a distinct substance, or by environmental conditions. Examples of suitable pharmaceutically active agents include vitamin B12, a bisphosphonate, taxol, Caspofungin, or an aminoglycoside antibiotic.

The terms "pharmaceutically active agent" and "therapeutic agent" are used interchangeably herein to refer to a chemical material or compound, which, when administered to an organism, induces a detectable pharmacologic and/or physiologic effect.

The compositions according to the present invention are characterized by the fact that their penetration capacity is virtually independent of the nature of the effector that is included in it.

"Counter ions" according to this invention can include also anionic or cationic amphipathic molecules, i.e., those having both polar and nonpolar domains, or both hydrophilic and hydrophobic properties. Anionic or cationic counter ions of this invention are ions that are negatively (anionic) or positively (cationic) charged and can include a hydrophobic moiety. Under appropriate conditions, anionic or cationic counter ions can establish electrostatic interactions with cationic or anionic impermeable molecules, respectively. The formation of such a complex can cause charge neutralization, thereby creating a new uncharged entity, with further hydrophobic properties in case of an inherent hydrophobicity of the counter ion.

Suitable anionic counter ions are ions with negatively charged residues such as carboxylate, sulfonate or phosphonate anions, and can further contain a hydrophobic moiety. Examples of such anionic counter ions include sodium dodecyl sulphate, dioctyl sulfosuccinate and other anionic compounds derived from organic acids.

Ionic liquids are salts composed of cations such as imidazolium ions, pyridinium ions and anions such as $BF_4^-$, $PF_6^-$ and are liquid at relatively low temperatures. Ionic liquids are characteristically in liquid state over extended temperature ranges, and have high ionic conductivity. When an ionic liquid is used as a reaction solvent, the solute is solvated by ions only, thus creating a totally different environment from that when water or ordinary organic solvents are used. This enables high selectivity, applications of which are steadily expanding.

Suitable cationic counter ions include quaternary amine derivatives, such as benzalkonium derivatives or other quaternary amines, which can be substituted by hydrophobic residues. In general, quaternary amines contemplated by the invention have the structure: 1-R1-2-R2-3-R3-4-R4-N, wherein R1, 2, 3, or 4 are alkyl or aryl derivatives. Further, quaternary amines can be ionic liquid forming cations, such as imidazolium derivatives, pyridinium derivatives, phosphonium compounds or tetraalkylammonium compounds.

For example, imidazolium derivatives have the general structure of 1-R1-3-R2-imidazolium where R1 and R2 can be linear or branched alkyls with 1 to 12 carbons. Such imidazolium derivatives can be further substituted for example by halogens or an alkyl group. Specific imidazolium derivatives include, but are not limited to, 1-ethyl-3-methylimidazolium, 1-butyl-3-methylimidazolium, 1-hexyl-3-methylimidazolium, 1-methyl-3-octylimidazolium, 1-methyl-3-(3,3,4,4,5,5,6,6,7,7,8,8,8-tridecafluorooctyl)-imidazolium, 1,3-dimethylimidazolium, and 1,2-dimethyl-3-propylimidazolium.

Pyridinium derivatives have the general structure of 1-R1-3-R2-pyridinium where R1 is a linear or branched alkyl with 1 to 12 carbons, and R2 is H or a linear or branched alkyl with 1 to 12 carbons. Such pyridinium derivatives can be further substituted for example by halogens or an alkyl group. Pyridinium derivatives include, but are not limited to, 3-methyl-1-propylpyridinium, 1-butyl-3-methylpyridinium, and 1-butyl-4-methylpyridinium.

The penetration compositions of this invention can further comprise a surface active agent. As described above, suitable surface active agents include ionic and non-ionic detergents. Examples of ionic detergents are fatty acid salts, lecithin, and bile salts. Examples of fatty acid salts are sodium octanoate, sodium decanoate, and sodium dodecanoate. Examples of non-ionic detergents include cremophore, a polyethylene glycol fatty alcohol ether, a sorbitan fatty acid ester, Solutol HS15, or a poloxamer. Examples of sorbitan fatty acid esters include sorbitan monolaurate, sorbitan monooleate, and sorbitan monopalmitate.

The penetration compositions of this invention may also contain adhesive polymers such as methylcellulose, ethylcellulose, hydroxypropylmethylcellulose (HPMC), or carbopol. Such adhesive polymers may assist in the consolidation of the formulation and/or help its adherence to mucosal surfaces. Additionally, the penetration compositions of this invention may also contain a monoglyceride. Examples of monoglycerides include glyceryl monooctanoate, glyceryl monodecanoate, glyceryl monolaurate, glyceryl monomyristate, glyceryl monostearate, glyceryl monopalmitate, and glyceryl monooleate.

The penetration compositions of this invention may further comprise a protective agent. An example of a protective agent is a protease inhibitor. Suitable protease inhibitors that can be added to the penetration composition are described in Bernkop-Schnurch et al., *J. Control. Release,* 52:1-16 (1998). These include, for example, inhibitors of luminally secreted proteases, such as aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly(acrylate) derivatives, chymostatin, benzyloxycarbonyl-Pro-Phe-CHO, FK-448, sugar biphenylboronic acids complexes, β-phenylpropionate, elastatinal, methoxysuccinyl-Ala-Ala-Pro-Val-chloromethylketone (MPCMK), EDTA, and chitosan-EDTA conjugates. These also include inhibitors of membrane bound proteases, such as amino acids, di- and tripeptides, amastatin, bestatin, puromycin, bacitracin, phosphinic acid dipeptide analogues, α-aminoboronic acid derivatives, Na-glycocholate, 1,10-phenanthroline, acivicin, L-serine-borate, thiorphan, and phosphoramidon.

Also included in the invention are methods of producing the compositions described herein. For example, in one embodiment the effector can be dissolved or suspended in a hydrophilic or partially hydrophilic solvent that is further immersed in a hydrophobic medium with a membrane fluidizing agent, thereby producing a composition contemplated by the invention. Alternatively, the effector, or any combination of effector and protein stabilizers forming the water soluble composition can be lyophilized together and then suspended with a membrane fluidizing agent in a hydrophobic medium. Other components of the composition can also be optionally lyophilized or added during reconstitution of the lyophilized materials.

It is well known to those skilled in the art that proteins can be further chemically modified to enhance the protein half-life in circulation. By way of non-limiting example, polyethylene glycol (PEG) residues can be attached to the effectors of the invention. Conjugating biomolecules with PEG, a process known as pegylation, is an established method for increasing the circulating half-life of proteins. Polyethylene glycols are nontoxic water-soluble polymers that, because of their large hydrodynamic volume, create a shield around the pegylated molecule, thereby protecting it from renal clearance, enzymatic degradation, as well as recognition by cells of the immune system.

Agent-specific pegylation methods have been used in recent years to produce pegylated molecules (e.g., drugs, proteins, agents, enzymes, etc.) that have biological activity that is the same as, or greater than, that of the "parent" molecule. These agents have distinct in vivo pharmacokinetic and pharmacodynamic properties, as exemplified by the self-regulated clearance of pegfilgrastim, the prolonged absorption half-life of pegylated interferon alpha-2a. Pegylated molecules have dosing schedules that are more convenient and more acceptable to patients, which can have a beneficial effect on the quality of life of patients. (See e.g., Yowell S. L. et al., Cancer Treat Rev 28 Suppl. A:3-6 (April 2002)).

The invention also includes methods of contacting biological barriers with compositions of the invention in an amount sufficient to enable efficient penetration through the barrier. The composition of this invention can be provided in vitro, ex vivo, or in vivo. Furthermore, the compositions according to this invention may be capable of improving the biological activity of the included substance. Therefore, another purpose of this invention is a method of using compositions to increase the biological activity of the effector.

In addition to the effector of the penetration composition, the invention also provides a pharmaceutically acceptable base or acid addition salt, hydrate, ester, solvate, prodrug, metabolite, stereoisomer, or mixture thereof. The invention also includes pharmaceutical formulations comprising penetration compositions in association with a pharmaceutically acceptable carrier, diluent, protease inhibitor, surface active agent, or excipient. A surface active agent can include, for example, poloxamers, Solutol HS15, cremophore, phospholipids, or bile acids/salts.

Salts encompassed within the term "pharmaceutically acceptable salts" refer to non-toxic salts of the compounds of this invention, which are generally prepared by reacting the free base with a suitable organic or inorganic acid or solvent to produce "pharmaceutically-acceptable acid addition salts" of the compounds described herein. These compounds retain the biological effectiveness and properties of the free bases. Representative examples of such salts include the water-soluble and water-insoluble salts, such as the acetate, amsonate (4,4-diaminostilbene-2,2'-disulfonate), benzenesulfonate, benzoate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

According to the methods of the invention, a patient, i.e., a human or an animal, can be treated with a pharmacologically or therapeutically effective amount of a composition of this invention. As used herein the term "pharmacologically or therapeutically effective amount" means that amount of a drug or pharmaceutical agent (the effector) that will elicit the biological or medical response of a tissue, system, animal or human that is being sought by a researcher or clinician.

The invention also includes pharmaceutical compositions suitable for introducing an effector of interest across a biological barrier. The compositions are preferably suitable for internal use and include an effective amount of a pharmacologically active compound of the invention, alone or in combination, with one or more pharmaceutically acceptable carriers. The compounds are especially useful in that they have very low, if any, toxicity.

Preferred pharmaceutical compositions are tablets and gelatin or hydroxypropylmethylcellulose ("HPMC") capsules, enteric coated, comprising the active ingredient together with a) diluents, e.g., lactose, dextrose, sucrose, mannitol, sorbitol, cellulose and/or glycine; b) protease inhibitors including, but not limited to, aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly(acrylate) derivatives, chymostatin, benzyloxycarbonyl-Pro-Phe-CHO; FK-448, sugar biphenylboronic acids complexes, β-phenylpropionate, elastatinal, methoxysuccinyl-Ala-Ala-Pro-Val-chloromethylketone ("MPCMK"), EDTA, chitosan-EDTA conjugates, amino acids, di-peptides, tripeptides, amastatin, bestatin, puromycin, bacitracin, phosphinic acid dipeptide analogues, α-aminoboronic acid derivatives, Na-glycocholate, 1,10-phenanthroline, acivicin, L-serine-borate, thiorphan, and phosphoramidon; c) lubricants, e.g., silica, talcum, stearic acid, its magnesium or calcium salt, poloxamer and/or polyethyleneglycol; for tablets also d) binders, e.g., magnesium aluminum silicate, starch paste, gelatin, tragacanth, methylcellulose, sodium carboxymethylcellulose and/or polyvinylpyrrolidone; if desired e) disintegrants, e.g., starches, agar, alginic acid or its sodium salt, or effervescent mixtures; and/or f) absorbents, colorants, flavors and sweeteners. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.001 to 75%, preferably about 0.01 to 10%, of the active ingredient.

Administration of the active compounds and salts described herein can be via any of the accepted modes of administration for therapeutic agents. These methods include oral, buccal, anal, rectal, bronchial, pulmonary, nasal, sublingual, intraorbital, parenteral, transdermal, or topical administration modes. As used herein "parenteral" refers to injections given through some other route than the alimentary canal, such as subcutaneously, intramuscularly, intraorbitally (i.e., into the eye socket or behind the eyeball), intracapsularly, intraspinally, intrasternally, or intravenously.

Depending on the intended mode of administration, the compositions may be in solid, semi-solid or liquid dosage form, such as, for example, tablets, emulsions, creams, ointments, suppositories, pills, time-release capsules, powders, liquids, suspensions, spray, aerosol or the like, preferably in unit dosages. The compositions will include an effective amount of active compound or the pharmaceutically acceptable salt thereof, and in addition, may also include any conventional pharmaceutical excipients and other medicinal or pharmaceutical drugs or agents, carriers, adjuvants, diluents, protease inhibitors, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid compositions can, for example, be prepared by dissolving, dispersing, emulsifying, etc. The active compound is dissolved in or mixed with a pharmaceutically pure solvent such as, for example, water, saline, aqueous dextrose, glycerol, propylene glycol, ethanol, and the like, to thereby form the solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Those skilled in the art will recognize that the penetration compositions of the present invention can also be used for mucosal vaccination, i.e., oral, nasal, rectal, vaginal, or bronchial, vaccine having an antigen, to which vaccination is desired, serve as the effector. Such a vaccine can include a composition including a desired antigenic sequence, including, but not limited to, the protective antigen (PA) component of Anthrax, or the Hepatitis B surface antigen (HBs) of Hepatitis B. This composition can then be orally or nasally administered to a subject in need of vaccination. The composition for mucosal vaccination can be administered to humans and also to other animals. These are referred to in general as "subjects" or "patients". Such animals include farm animals such as cattle, sheep, goats, horses, chickens, and also cats, dogs, and any other animal in veterinary care.

An "antigen" is a molecule or a portion of a molecule capable of stimulating an immune response, which is additionally capable of inducing an animal or human to produce antibody capable of binding to an epitope of that antigen. An "epitope" is that portion of any molecule capable of being recognized by and bound by a major histocompatibility complex ("MHC") molecule and recognized by a T cell or bound by an antibody. A typical antigen can have one or more than one epitope. The specific recognition indicates that the antigen will react, in a highly selective manner, with its corresponding MHC and T cell, or antibody and not with the multitude of other antibodies that can be evoked by other antigens.

A peptide is "immunologically reactive" with a T cell or antibody when it binds to an MHC and is recognized by a T cell or binds to an antibody due to recognition (or the precise fit) of a specific epitope contained within the peptide. Immunological reactivity can be determined by measuring T cell response in vitro or by antibody binding, more particularly by the kinetics of antibody binding, or by competition in binding using known peptides containing an epitope against which the antibody or T cell response is directed, as competitors.

Techniques used to determine whether a peptide is immunologically reactive with a T cell or with an antibody are known in the art. Peptides can be screened for efficacy by in vitro and in vivo assays. Such assays employ immunization of an animal, e.g., a mouse, a rabbit or a primate, with the peptide, and evaluation of the resulting antibody titers.

Also included within the invention are vaccines that can elicit the production of secretory antibodies (IgA) against the corresponding antigen, as such antibodies serve as the first line of defense against a variety of pathogens. Mucosal vaccination, which has the advantage of being a non-invasive route of administration, and is the preferred means of immunization for obtaining secretory antibodies, although the vaccination can be administered in a variety of ways, e.g., orally, topically, or parenterally, i.e., subcutaneously, intraperitoneally, by viral infection, intravascularly, etc.

The compositions of the present invention can be administered in oral dosage forms such as tablets, capsules (each including timed release and sustained release formulations), pills, powders, granules, elixirs, tinctures, suspensions, syrups, creams, sprays and emulsions. The compositions of the present invention can also be administered in nasal dosage forms such as sprays, gels, emulsions or creams.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, may be provided in the form of scored tablets or capsules containing 0.001, 0.0025, 0.005, 0.01, 0.025, 0.05, 0.1, 0.25, 0.5, 1.0, 2.5, 5.0, 10.0, 15.0, 25.0, 50.0, 100.0, 250.0, 500.0 or 1000.0 mg of active ingredient.

Compounds of the present invention may be administered in a single daily dose, or the total daily dosage may be administered in divided doses of two, three or four times daily.

Furthermore, preferred compounds for the present invention can be administered in buccal form via topical use of suitable buccal vehicles, bronchial form via suitable aerosols or inhalants, intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.001% to 50%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, propylene glycol, glycerol, water and the like. Moreover, when desired or necessary, suitable binders, lubricants, protease inhibitors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, poloxamer, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methylcellulose, agar, bentonite, xanthan gum and the like.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above compositions may contain 0.001-99%, preferably 0.01-50% of the active compounds as active ingredients.

The following EXAMPLES are presented in order to more fully illustrate the preferred embodiments of the invention. These EXAMPLES should in no way be construed as limiting the scope of the invention, as defined by the appended claims.

EXAMPLES

Example 1

Utilization of Compositions of the Instant Invention to Enable the Effective Translocation of Insulin Across an Epithelial Barrier a) Measurement of Blood Glucose Levels in Rats:

A composition contemplated by the instant invention was prepared by dissolving human insulin with spermine and phytic acid in double distilled water ("DDW") containing NaOH. The solution was then lyophilized and suspended with sodium dodecanoate (SD), octanol and geraniol in a mixture of mineral oil, medium chain triglyceride (MCT) oil and castor oil. Components and concentrations are detailed in Table 1.

TABLE 1

Composition for insulin translocation

| h-Insulin in 7 mM NaOH in DDW (pH 9.0) | Spermine (50 mg/ml in DDW) | Phytic acid (50 mg/ml in DDW) | Lyophilization | 10% SD in Propylene Glycol | Octanol:Geraniol 1:1 | Mineral oil:MCT:Castor oil 1:1:1 | Sonication | Insulin concentration |
|---|---|---|---|---|---|---|---|---|
| 1 mg/985 μl | 0.5 mg (10 μl) | 0.25 mg (5 μl) | | 90 μl | 90 μl | 820 μl | 30" | 1 mg/ml |

Eight male SD rats, 175-200 gr, were deprived of food, 18 hours prior to the experiment. The animals were divided into 2 groups, and anesthetized by a solution of 85% ketamine, 15% xylazine, 0.1 ml/100 g of body weight. Each preparation was administered either i.m. (100 ul/rat, containing 1.11 IU insulin) or rectally (100 ul/rat, containing 2.8 IU insulin). Rectal administration was done by gently inserting through the rectal orifice a plastic canule protected by a soft coating, to a depth of 2 cm. Blood glucose levels were measured at various time intervals post administration, in blood samples drawn from the tip of the tail. (See FIG. 1).

As can be seen in FIG. 1, after the composition was administered rectally, glucose levels dropped gradually and significantly, indicating insulin absorption from the intestine into the blood stream.

b) Measurement of Serum Insulin Levels in Rats:

The composition was prepared by dissolving human insulin with spermine and phytic acid in DDW containing NaOH. The solution was then lyophilized and suspended with sodium dodecanoate (SD), octanol and geraniol in a mixture of mineral oil, medium chain triglyceride (MCT) oil and castor oil. Components and concentrations are detailed in Table 2.

TABLE 2

Composition for insulin translocation

| h-Insulin in 7 mM NaOH in DDW (pH 9.0) | Spermine (50 mg/ml in DDW) | Phytic acid (50 mg/ml in DDW) | Lyophilization | 10% SD in Propylene Glycol | Octanol:Geraniol 1:1 | Mineral oil:MCT:Castor oil 1:1:1 | Sonication | Insulin concentration |
|---|---|---|---|---|---|---|---|---|
| 1 mg/985 μl | 0.5 mg (10 μl) | 0.25 mg (5 μl) | | 90 μl | 90 μl | 820 μl | 30" | 1 mg/ml |

Eight male SD rats, 175-200 gr, were deprived of food, 18 hours prior to the experiment. The animals were divided into 2 groups, and anesthetized by a solution of 85% ketamine, 15% xylazine, 0.1 ml/100 g of body weight. Each preparation was administered either i.m. (100 ul/rat, containing 1.11 IU insulin) or rectally (100 ul/rat, containing 2.8 IU insulin). Rectal administration was done by gently inserting through the rectal orifice a plastic canule protected by a soft coating, to a depth of 2 cm. Blood glucose levels were measured at various time intervals post administration, in blood samples drawn from the tip of the tail. Additionally, an insulin radio-immunoassay was performed to assess insulin levels in the serum. (See Table 3).

TABLE 3

| | | glucose (mg/dL) and insulin(μU), time post administration | | | | | | | |
|---|---|---|---|---|---|---|---|---|---|
| | route of administration | 0 | 5 | 10 | 20 | 30 | 45 | 60 | 90 |
| rat # 5 | blood glucose (mg/dL) | 75 | 84 | 78 | 56 | 49 | 21 | 18 | 23 |
| i.m. | glucose (%) | 100 | 112.00 | 104.00 | 74.67 | 65.33 | 28.00 | 24.00 | 30.67 |
| | insulin, 25 ul | 15.49 | 103.6 | 81.82 | 78.41 | 110.55 | 86.53 | 86.08 | 13.73 |
| rat # 6 | blood glucose (mg/dL) | 78 | 89 | 87 | 63 | 48 | 25 | 22 | 26 |
| i.m. | glucose (%) | 100 | 114.10 | 111.54 | 80.77 | 61.54 | 32.05 | 28.21 | 33.33 |
| | insulin, 25 ul | 19.37 | 63.22 | 80.98 | 42.75 | 41.31 | 49.25 | 58.54 | 57.51 |
| rat # 7 | blood glucose (mg/dL) | 84 | 90 | 81 | 56 | 39 | 18 | 18 | 18 |
| i.m. | glucose (%) | 100 | 107.14 | 96.43 | 66.67 | 46.43 | 21.43 | 21.43 | 21.43 |
| | insulin, 25 ul | 20.36 | 153.22 | 135.29 | 152.57 | 114.8 | 133.38 | 122.7 | 20.01 |
| rat # 8 | blood glucose (mg/dL) | 80 | 79 | 78 | 77 | 63 | 52 | 41 | 38 |
| i.m. | glucose (%) | 101 | 98.75 | 97.50 | 96.25 | 78.75 | 65.00 | 51.25 | 47.50 |
| | insulin, 25 ul | 7.17 | 32.37 | 31.98 | 28.49 | 19.37 | 19.16 | 19.52 | 18.31 |

TABLE 3-continued

|  | route of administration | glucose (mg/dL) and insulin(μU), time post administration | | | | | | | |
|---|---|---|---|---|---|---|---|---|---|
|  |  | 0 | 5 | 10 | 20 | 30 | 45 | 60 | 90 |
| rat # 1 | blood glucose (mg/dL) | 74 | 85 | 77 | 61 | 43 | 34 | 28 | 42 |
| rectal | glucose (%) | 100 | 114.86 | 104.05 | 82.43 | 58.11 | 45.95 | 37.84 | 56.76 |
|  | insulin, 25 ul | 14.08 | 119.41 | 118.49 | 46.99 | 25.79 | 26.36 | 20 | 10 |
| rat # 2 | blood glucose (mg/dL) | 60 | 82 | 73 | 57 | 41 | 32 | 24 | 36 |
| rectal | glucose (%) | 100 | 136.67 | 121.67 | 95.00 | 68.33 | 53.33 | 40.00 | 60.00 |
|  | insulin, 25 ul | 10.42 | 99.71 | 88.98 | 48.39 | 35.3 | 30.32 | 46.069 | 19.48 |
| rat # 3 | blood glucose (mg/dL) | 67 | 83 | 81 | 64 | 39 | 30 | 37 | 54 |
| rectal | glucose (%) | 100 | 123.88 | 120.90 | 95.52 | 58.21 | 44.78 | 55.22 | 80.60 |
|  | insulin, 25 ul | 19.3 | 83.38 | 114.59 | 32.9 | 24.56 | 21.69 | 13.87 | 14.63 |
| rat # 4 | blood glucose (mg/dL) | 63 | 78 | 75 | 61 | 46 | 23 | 18 | 23 |
| rectal | glucose (%) | 101 | 123.81 | 119.05 | 96.83 | 73.02 | 36.51 | 28.57 | 36.51 |
|  | insulin, 25 ul | 12.98 | 141.25 | 210.18 | 92 | 53.04 | 37.29 | 40.78 | 16.14 |

Blood glucose levels decrease in relation to the amount of insulin absorbed from the intestine into the bloodstream (i.e., in an amount that correlates to the amount of insulin absorbed). Thus, this drug delivery system can replace the need for insulin injections, thereby providing an efficient, safe and convenient route of administration for diabetes patients.

c) Measurement of Blood Glucose and Serum Insulin Levels in Pigs:

A composition was prepared by dissolving human insulin with spermine and polyvinylpyrrolidone (PVP-40), sodium dodecanoate (SD) and methylcellulose (MC-400) in DDW containing NaOH. The solution was then lyophilized and suspended with octanol and geraniol in a mixture of medium chain triglyceride (MCT) oil and castor oil, further containing sorbitan monopalmitate (Span-40). Components and concentrations are detailed in Table 4.

TABLE 4

Composition for insulin translocation

| h-Insulin in 7 mM NaOH in DDW (pH 9.0) | Spermine (50 mg/ml in DDW) | PVP-40, (200 mg/ml in DDW) | 10% SD in Propylene Glycol | 0.2% MC-400 | Lyophilization | Geraniol:Octanol (1:1) | 1% Span-40 in MCT:Castor oil (1:2) | Sonication |
|---|---|---|---|---|---|---|---|---|
| 1 mg/985 μl | 0.5 mg | 5 mg | 9 mg | 1 mg |  | 100 μl | 900 μl | 30" |

Six female mini-pigs, 45-50 kg, were deprived of food, 18 hours prior to the experiment. The animals were divided into 2 groups, and anesthetized by a solution of 66% ketamine, 33% xylazine, 0.3 ml/kg of body weight. The superior vena cava was canulated transdermally to facilitate blood collection. Each preparation was administered either i.m. (0.22 IU/kg insulin) or rectally (1.1 IU/kg insulin). Rectal administration was done by gently inserting through the rectal orifice a plastic syringe, to a depth of 2 cm. Blood glucose levels were measured at various time intervals post administration, and an insulin radioimmunoassay was performed to assess insulin levels in the serum. (See Table 5).

TABLE 5

| Pig # | route of administration | glucose (mg/dL) and insulin(μU), time post administration | | | | | | | |
|---|---|---|---|---|---|---|---|---|---|
|  |  | 0 | 5 | 10 | 20 | 30 | 45 | 60 | 90 |
| 519 | blood glucose (mg/dL) | 87 | 82 | 84 | 71 | 64 | 55 | 48 | 39 |
| SCD, i.m. | glucose (%) | 100 | 94.25 | 96.55 | 81.61 | 73.56 | 63.22 | 55.17 | 44.83 |
|  | insulin, 100 ul | 14.74 | 34.95 | 36.9 | 31.57 | 32.81 | 41.09 | 32.07 | 36.71 |
| 526 | blood glucose (mg/dL) | 47 | 47 | 40 | 30 | 22 | 18 | 18 | 18 |
| SCD, i.m. | glucose (%) | 100 | 100.00 | 85.11 | 63.83 | 46.81 | 38.30 | 38.30 | 38.30 |
|  | insulin, 100 ul | 31.56 | 65.51 | 84.88 | 54.93 | 61.47 | 57.62 | 52.83 | 48.07 |
| 518 | blood glucose (mg/dL) | 54 | 55 | 52 | 48 | 38 | 31 | 21 | 22 |
| SCD, rectal | glucose (%) | 100 | 101.85 | 96.30 | 88.89 | 70.37 | 57.41 | 38.89 | 40.74 |
|  | insulin, 100 ul | 21.11 | 71.56 | 60.92 | 89.19 | 64.12 | 23.29 | 32.4 | 21.45 |
| 520 | blood glucose (mg/dL) | 104 | 95 | 95 | 84 | 57 | 31 | 18 | 22 |
| SCD, rectal | glucose (%) | 100 | 91.35 | 91.35 | 80.77 | 54.81 | 29.81 | 17.31 | 21.15 |
|  | insulin, 100 ul | 8.99 | 170.96 | 124.38 | 189.6 | 166.58 | 76.96 | 68.06 | 24.67 |

TABLE 5-continued

| Pig # | route of administration | glucose (mg/dL) and insulin(µU), time post administration | | | | | | | |
|---|---|---|---|---|---|---|---|---|---|
| | | 0 | 5 | 10 | 20 | 30 | 45 | 60 | 90 |
| 525 | blood glucose (mg/dL) | 73 | 77 | 75 | 51 | 32 | 20 | 18 | 24 |
| SCD, rectal | glucose (%) | 100 | 105.48 | 102.74 | 69.86 | 43.84 | 27.40 | 24.66 | 32.88 |
| | insulin, 100 ul | 38.23 | 63.65 | 146.43 | 94.39 | 51.07 | 26.99 | 22.27 | 15.86 |
| 527 | blood glucose (mg/dL) | 72 | 68 | 68 | 51 | 28 | 18 | 18 | 21 |
| SCD, rectal | glucose (%) | 100 | 94.44 | 94.44 | 70.83 | 38.89 | 25.00 | 25.00 | 29.17 |
| | insulin, 100 ul | 11.83 | 60.06 | 116.63 | 95.79 | 42.2 | 27.03 | 25.85 | 25 |

As can be seen in Table 5, after the composition was administered rectally, glucose levels dropped gradually and significantly, alongside the rise in serum insulin levels, indicating insulin absorption from the intestine into the blood stream.

d) Measurement of Blood Glucose and Serum Insulin Levels in Streptozotocin-Induced Diabetic Rats:

The composition prepared by dissolving human insulin with spermine, polyvinylpyrrolidone (PVP-40), and sodium dodecanoate (SD) in DDW containing NaOH, octanol and geraniol. The solution was then lyophilized and suspended with an additional amount of octanol and geraniol in a mixture of medium chain triglyceride (MCT) oil and castor oil further containing sorbitan monopalmitate (Span-40), methylcellulose (MC-400), and glyceryl monooleate (GMO). Components and concentrations are detailed in Table 6.

TABLE 6

Composition for insulin translocation

| h-Insulin in 7 mM NaOH in DDW (pH 9.0) | Spermine (50 mg/ml in DDW) | PVP-40 (200 mg/ml in DDW) | 10% SD in DDW | Geraniol | Octanol | Lyophilization | Geraniol | Octanol | 1% Span-40, 2% GMO, 0.2% MC-400 in MCT:Castor Oil 1:2 | Sonication, | Insulin concentration |
|---|---|---|---|---|---|---|---|---|---|---|---|
| 4 mg/ 3 ml | 2 mg (40 µl) | 20 mg (100 µl) | 180 µl | 20 µl | 20 µl | | 150 µl | 150 µl | 700 µl | 40" | 4 mg/ml |

Insulin-dependant diabetes was induced by i.v. injection of streptozotocin (50 mg/kg) to the tail vein of six male SD rats, 200-250 gr. Diabetic state was confirmed by measurements of fasting blood glucose levels of 300-400 mg/dL, 72 hrs after streptozotocin injection.

Five such diabetic rats were deprived of food, 18 hours prior to the experiment. The animals were divided into 2 groups, and anesthetized by a solution of 85% ketamine, 15% xylazine, 0.1 ml/100 g of body weight. Each preparation was administered either i.m. (100 ul/rat, containing 0.56 IU insulin) or rectally (100 ul/rat, containing 11.2 IU insulin). Rectal administration was done by gently inserting through the rectal orifice a plastic canule protected by a soft coating, to a depth of 2 cm. Blood glucose levels were measured at various time intervals post administration, in blood samples drawn from the tip of the tail. Additionally, an insulin radioimmunoassay was performed to assess insulin levels in the serum. (See Table 7).

TABLE 7

| | route of administration | glucose (mg/dL) and insulin(µU), time post administration | | | | | | |
|---|---|---|---|---|---|---|---|---|
| | | 0 | 5 | 10 | 20 | 30 | 45 | 60 |
| rat # 1 | glucose (mg/dL) | 242 | 270 | 223 | 205 | 220 | | 20 |
| SCD, rectal | glucose (%) | 100 | 111.57 | 92.15 | 84.71 | 90.91 | 0.00 | 8.26 |
| | insulin, 100 ul | 15.51 | 124.75 | 179.89 | 47.5 | 342.1 | | |
| rat # 2 | glucose (mg/dL) | 30 | 49 | 32 | 27 | 32 | 23 | 20 |
| SCD, rectal | glucose (%) | 100 | 163.33 | 106.67 | 90.00 | 106.67 | 76.67 | 66.67 |
| | insulin, 100 ul | 23.47 | 242.59 | 492.25 | 664.44 | 668.93 | 1687.44 | 423.36 |
| rat # 3 | glucose (mg/dL) | 437 | 411 | 411 | 398 | 378 | 377 | 358 |
| SCD, rectal | glucose (%) | 100 | 94.05 | 94.05 | 91.08 | 86.50 | 86.27 | 81.92 |
| | insulin, 100 ul | 26.35 | 288.24 | 408.6 | 299.75 | 597.4 | 387.62 | 593.73 |
| rat # 4 | glucose (mg/dL) | 437 | 401 | 402 | 398 | 406 | 380 | 373 |
| SCD, i.m. | glucose (%) | 100 | 91.76 | 91.99 | 91.08 | 92.91 | 86.96 | 85.35 |
| | insulin, 100 ul | 18.13 | 47.46 | 117.91 | 149.07 | 216.61 | 216.97 | 252.95 |
| rat # 5 | glucose (mg/dL) | 239 | 288 | 358 | 269 | 306 | 323 | 299 |
| SCD, i.m. | glucose (%) | 100 | 120.50 | 149.79 | 112.55 | 128.03 | 135.15 | 125.10 |
| | insulin, 100 ul | 18.49 | 50.79 | 56.61 | 76.92 | 113.47 | 52.93 | 116.72 |

As can be seen in Table 7, after the composition was administered rectally, glucose levels dropped gradually and significantly, alongside the rise in serum insulin levels, indicating insulin absorption from the intestine into the blood stream.

Example 2

Utilization of Compositions of the Instant Invention to Enable the Effective Translocation of Heparin Across an Epithelial Barrier The composition used for this study was prepared by dissolving human unfractionated heparin with spermine, and sodium dodecanoate in DDW containing NaOH. The solution was then lyophilized and suspended with octanol and geraniol in a mixture of medium chain triglyceride (MCT) oil and castor oil further containing sorbitan monopalmitate (Span-40), methylcellulose (MC-400), glyceryl monooleate, and pluronic (F-127). Components and concentrations are detailed in Table 8.

TABLE 8

Composition for heparin translocation

| Heparin | Spermine | SD | Lyophilization in 7 mM NaOH | Geraniol | Octanol | 1% Span-40, 2% GMO, 1% Pluronic F-127, 0.2% MC-400 in MCT:Castor Oil 1:2 |
|---|---|---|---|---|---|---|
| 10 mg | 5 mg | 180 µl | | 100 µl | 100 µl | 800 µl |

Five male CB6/F1 mice, 9-10 wks, were divided into 2 groups, and anesthetized by a solution of 85% ketamine, 15% xylazine, 0.01 ml/10 g of body weight. Each preparation was administered either i.p. (100 ul/mouse, containing 0.2 mg heparin) or rectally (100 ul/mouse, containing 1 mg heparin). Rectal administration was done by gently inserting through the rectal orifice a plastic canule protected by a soft coating, to a depth of 1 cm. Clotting times were measured at various time intervals post administration, in blood samples drawn from the tip of the tail into a glass capillary. (See Table 9).

TABLE 9

Clotting times following Heparin Administration to Mice

| | | clotting time (min), time post administration | | | | | |
|---|---|---|---|---|---|---|---|
| pH | route of administration | 0 | 5 | 15 | 30 | 45 | 60 | 90 |
| mouse # 1 | 1, i.p | 1 | 1 | 1 | 4 | 7 | 10 | 15 |
| mouse # 2 | 1, i.p | 1 | 6 | 5 | 10 | 14 | 9 | 10 |
| mouse # 3 | 1, rectal | 1 | 3 | 4 | 5 | 4 | 4 | 4 |
| mouse # 4 | 1, rectal | 1.5 | 3 | 6 | 11 | 14 | 16 | 14 |
| mouse # 5 | 1, rectal | 1 | 5 | 2 | 13 | 12 | 12 | 12 |

Clotting time values increase in relation to the amount of heparin absorbed from the intestine into the bloodstream (i.e., in an amount that correlates to the amount of heparin absorbed). Therefore, this drug delivery system will replace the use of heparin injections.

Example 3

Utilization of Compositions of the Instant Invention to Enable the Effective Translocation of Interferon Alpha Across an Epithelial Barrier A composition contemplated by the instant invention was prepared by dissolving human interferon alpha with spermine, polyvinylpyrrolidone (PVP-40) and sodium dodecanoate (SD) in DDW containing NaOH. The solution was then lyophilized and suspended with octanol and geraniol in a mixture of medium chain triglyceride (MCT) oil and castor oil further containing sorbitan monopalmitate (Span-40), methylcellulose (MC-400), and glyceryl monooleate (GMO). Components and concentrations are detailed in Table 10.

TABLE 10

Composition for interferon alpha translocation

| INF-α (200 µg/ml) in PBS | 7 mM NaOH in DDW | Spermine (50 mg/ml) in DDW) | PVP-40, (200 mg/ml in DDW) | 10% SD in DDW | Lyophilization | Geraniol | Octanol | 1% Span-40, 0.2% MC-400, 2% GMO, in MCT:Castor oil 1:2 | Sonication | INF-α concentration |
|---|---|---|---|---|---|---|---|---|---|---|
| 250 µl (50 µg) | 375 µl | 0.5 mg (10 µl) | 2.5 mg (25 µl) | 45 µl | | 25 µl | 25 µl | 450 µl | 30" | 100 µg/ml |

Six male SD rats, 175-200 gr were divided into 2 groups, and anesthetized by a solution of 85% ketamine, 15% xylazine, 0.1 ml/100 g of body weight. The external jugular veins were then exposed by removing the overlaying skin. The compositions were administered either nasally (25 ul/rat, containing 2.5 mcg interferon-alpha) or rectally (50 ul/rat, containing 5 mcg interferon-alpha). Nasal administration was done by smearing of the composition over the external nasal orifices. Rectal administration was done by gently inserting through the rectal orifice a plastic canule protected by a soft coating, to a depth of 2 cm. Blood samples were drawn from the jugular veins at various time intervals post administration (See FIGS. 2-3). Serum was analyzed for detection of IFN-alpha by an ELISA immunoassay.

Figure 2:
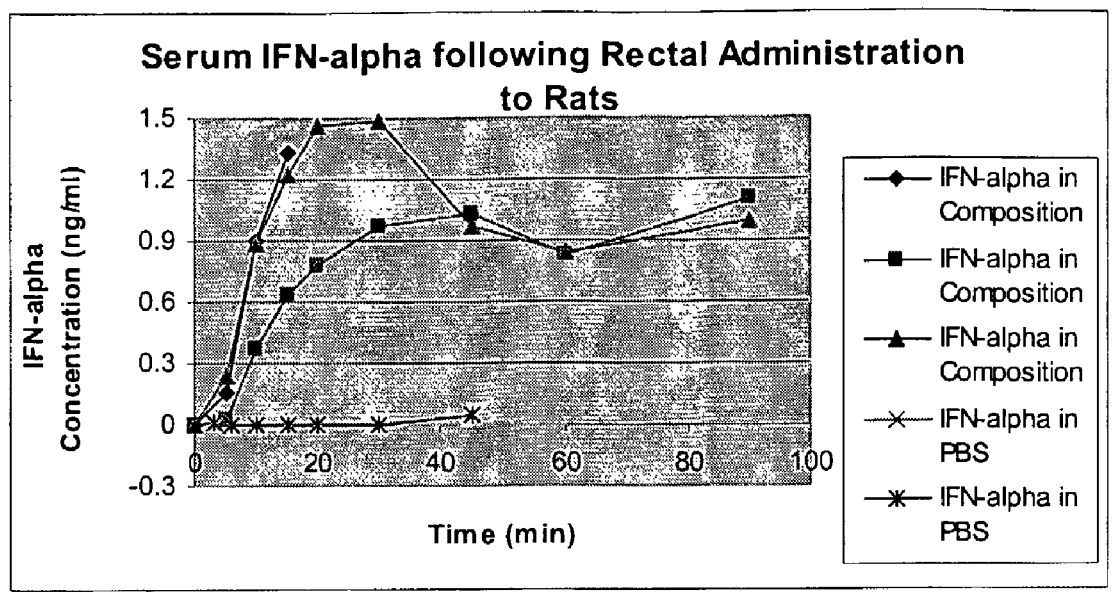
FIG. 2 depicts the significant concentrations of interferon alpha detected in the blood stream as a result of using the penetration composition of the invention to translocate interferon alpha across the intestine in rats, in comparison with a control solution of interferon alpha in phosphate buffered saline. Preparations were administered rectally, and serum samples were collected at various time intervals thereafter.
Figure 3:
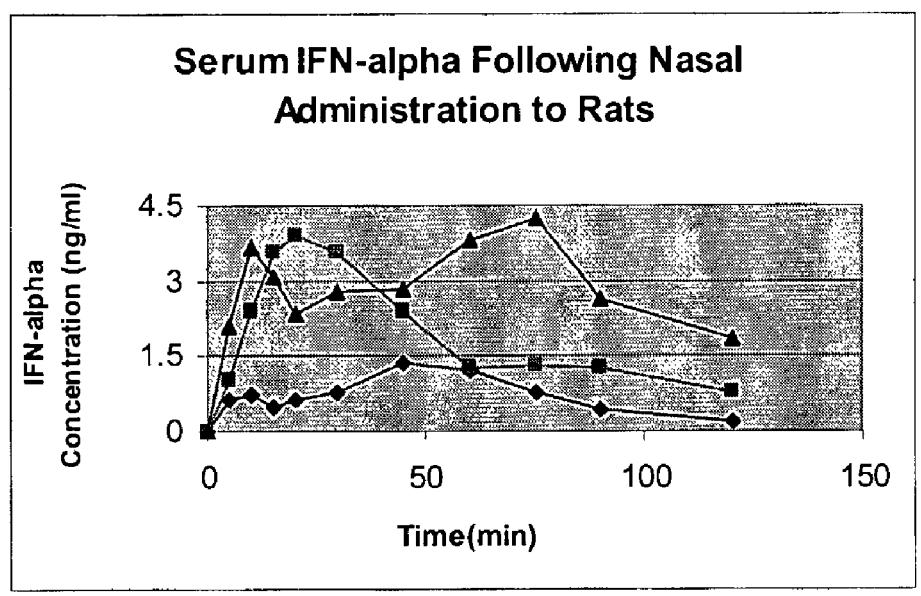
FIG. 3 depicts the significant concentrations of interferon alpha detected in the blood stream as a result of using the penetration composition of the invention to translocate interferon alpha across the nasal mucosa in rats. Preparations were administered nasally, and serum samples were collected at various time intervals thereafter.

As can be seen in FIGS. 2-3, both nasal and rectal administration of IFN-alpha result in significant levels of IFN-alpha in the blood stream, indicating interferon-alpha absorption from the intestine into the blood stream.

As a comparison, results of rectal administration of IFN-alpha dissolved in phosphate buffered saline are also shown in FIG. 2, utilizing equivalent amounts of IFN-alpha per rat. These show no IFN-alpha in the blood stream, and therefore no detected absorption from the intestine.

Example 4

Utilization of Compositions of the Instant Invention to Enable the Effective Translocation of GLP-1 Across an Epithelial Barrier A composition was prepared by dissolving human GLP-1 with spermine, polyvinylpyrrolidone (PVP-40), sodium dodecanoate, and methylcellulose (MC-400) in DDW containing NaOH. The solution was then lyophilized and suspended with octanol and geraniol in a mixture of medium chain triglyceride (MCT) oil and castor oil further containing sorbitan monopalmitate (Span-40). Components and concentrations are detailed in Table 11. The control composition was prepared as described above, without the GLP-1.

TABLE 11

| Composition for GLP-1 translocation | | | | | | | | |
|---|---|---|---|---|---|---|---|---|
| GLP-1 (7-36) amide in 7 mM NaOH | Spermine | PVP-40 | SD | MC-400 | Lyophilization | Geraniol | Octanol | 1% Span-40, in MCT:Castor oil 1:2 |
| 0.5 mg | 0.25 mg | 2.5 mg | 9 mg | 2 mg | | 50 μl | 50 μl | 900 μl |

Six male SD rats, 175-200 gr, were deprived of food, 18 hours prior to the experiment. The animals were divided into 3 groups, and each animal was given 200 mg glucose from a 50% glucose solution in water, by oral gavage. Ten minutes afterwards, each preparation was administered either i.p. (50 ul/rat, containing 25 mcg GLP-1) or rectally (200 ul/rat, containing 100 mcg GLP-1). Rectal administration was done by gently inserting through the rectal orifice a plastic canule protected by a soft coating, to a depth of 2 cm. Blood glucose levels were measured at various time intervals post administration, in blood samples drawn from the tip of the tail. (See FIG. 4).

Figure 4:
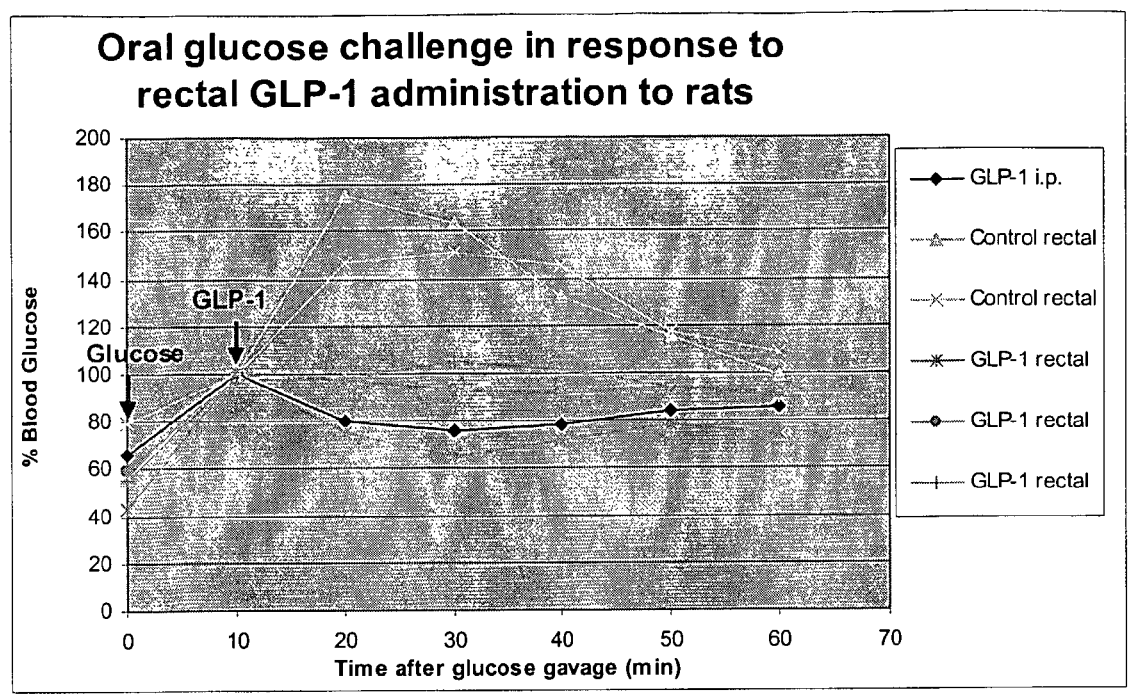
FIG. 4 depicts the attenuation of the response to an oral glucose challenge in rats, as a result of using the penetration composition of the invention to translocate GLP-1 across the intestine. Rats were administered an oral glucose load and then preparations were administered either i.p. or rectally, and also a control preparation without GLP-1, and blood glucose levels were measured at various time intervals thereafter.

As can be seen in FIG. 4, rectally administered GLP-1 attenuates the rise in blood glucose seen in the control animals, to a degree similar to that of parenterally administered GLP-1, indicating absorption from the intestine into the blood stream.

Example 5

Utilization of Compositions for Mucosal Vaccination

The composition used for mucosal vaccination contains a desired antigenic sequence, i.e., the PA antigen of Anthrax, and protein stabilizers, i.e., spermine and phytic acid, which can be dissolved and then lyophilized together, along with additional components such as polyvinylpyrrolidone and a surface active agent, i.e., Na dodecanoate, and then suspended with membrane fluidizing agents, i.e., octanol and geraniol, in a hydrophobic medium, i.e., a mixture of MCT oil or glyceryl tributyrate and castor oil. Additional possible components of the composition have been described. Such a composition can be administered nasally or orally to a subject in need of vaccination.

This method allows simple and rapid vaccination of large populations in need thereof. Another advantage of this method is the production of high titers of IgA antibodies and the subsequent presence of IgA antibodies in the epithelial mucosa, which are the sites of exposure to antigens.

Efficacy of vaccination can be demonstrated by the measurement of specific antibody titers, especially for IgA, as well as the measurement of immunological response to stimulation, such as for example, via a cutaneous hypersensitivity reaction in response to subcutaneous administration of antigen.

OTHER EMBODIMENTS

From the foregoing detailed description of the specific embodiments of the invention, it should be apparent that unique methods of translocation across epithelial and endothelial barriers have been described. Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims. For instance, the choice of the particular type of tissue, or the particular effector to be translocated is believed to be a matter of routine for a person of ordinary skill in the art with knowledge of the embodiments described herein.

I claim:

1. A method for producing an oral administration composition, the method comprising:
   (i) providing a therapeutically effective amount of at least one effector in an aqueous composition, wherein said aqueous composition comprises a fatty acid salt selected from: sodium octanoate, sodium decanoate, sodium dodecanoate, and combinations thereof and wherein said effector comprises a peptide;
   (ii) evaporating the aqueous composition by lyophilizing said aqueous composition to produce a lyophilizate comprising a water soluble composition comprising the fatty acid salt;
   (iii) suspending the lyophilizate comprising a water soluble composition comprising the fatty acid salt in a hydrophobic medium to produce a suspension, wherein said hydrophobic medium is selected from the group consisting of aliphatic molecules, cyclic molecules, aromatic molecules and combinations thereof; and
   (iv) further comprising a lecithin, a bile salt or a non-ionic detergent.

2. The method of claim 1, wherein said at least one peptide effector comprises an impermeable molecule selected from the group consisting of: insulin; erythropoietin (EPO); glucagon-like peptide 1 (GLP-1); melanocyte stimulating hormone (αMSH); parathyroid hormone (PTH); peptide YY amino acids 3-36 (PYY(3-36)); interleukin-2 (IL-2); a 1-antitrypsin; granulocyte/monocyte colony stimulating factor (GM-CSF); granulocyte colony stimulating factor (G-CSF); T20; anti-TNF antibodies; interferon α; interferon β; interferon γ; luteinizing hormone releasing hormone (LHRH) analog; brain-derived natriuretic peptide (BNP); a hormone; a growth factor; an incretin; a neurotrophic factor; an antibody; a monoclonal antibody; an antibody fragment; an immunomodulator; a soluble receptor; an enzyme; and Caspofungin.

3. The method of claim 1, wherein said fatty acid salt is sodium octanoate.

4. The method of claim 1, wherein said aliphatic molecules are selected from the group consisting of: mineral oil, paraffin, fatty acids, mono-glycerides, di-glycerides, tri-glycerides, such as long chain triglycerides, medium chain triglycerides, short chain triglycerides, ethers, and esters, wherein said cyclic hydrophobic medium is selected from the group consisting of: terpenoids, cholesterol, cholesterol derivatives such as cholesterol sulfate, and cholesterol esters of fatty acids, or wherein said aromatic hydrophobic medium is benzyl benzoate.

5. The method of claim 4, wherein said aliphatic molecules are medium chain triglycerides.

6. The method of claim 4, wherein said long chain triglyceride is castor oil.

7. The method of claim 4, wherein said short chain triglyceride is glyceryl tributyrate.

8. The method of claim 1, wherein said water soluble composition further comprises a stabilizer.

9. The method of claim 8, wherein said water soluble composition further comprises polyvinylpyrrolidone.

10. The method of claim 8, wherein said water soluble composition further comprises polyvinylalcohol.

11. The method of claim 1, wherein said at least one peptide effector comprises an impermeable molecule selected from the group consisting of: parathyroid hormone amino acids 1-34 (PTH 1-34); growth hormone; calcitonin; luteinizing hormone (LH); follicle-stimulating hormone (FSH); enkephalin; dalargin; kytotorphin; basic fibroblast growth factor (bFGF); hirudin and hirulog.

12. An oral administration composition obtained by the method of claim 1, the composition comprising:
  (i) a therapeutically effective amount of at least one effector in an aqueous composition, wherein said aqueous composition comprises a fatty acid salt selected from: sodium octanoate, sodium decanoate, sodium dodecanoate, and combinations thereof, and wherein said effector comprises a peptide;
  (ii) a lyophilizate comprising a water soluble composition comprising the fatty acid salt;
  (iii) a hydrophobic medium, wherein said hydrophobic medium is selected from the group consisting of aliphatic molecules, cyclic molecules, aromatic molecules and combinations thereof; and
  (iv) a lecithin, a bile salt or a non-ionic detergent.

13. The therapeutic composition of claim 12, comprising a non-ionic detergent.

14. The therapeutic composition of claim 13, wherein the non-ionic detergent is a cremophore, a polyethylene glycol fatty alcohol ether, Solutol HS15, a poloxamer or a sorbitan fatty acid ester.

15. The therapeutic composition of claim 14, wherein the non-ionic detergent is a sorbitan fatty acid ester.

16. The therapeutic composition of claim 12, wherein the composition further comprises a monoglyceride.

17. The therapeutic composition of claim 16, wherein the monoglyceride is glyceryl monooctanoate.

18. The therapeutic composition of claim 12, which further comprises an alcohol selected from the group consisting of linear alcohols, branched alcohols, cyclical alcohols, aromatic alchohols and combinations thereof.

19. The therapeutic composition of claim 12, wherein said composition is contained within a capsule.

20. The therapeutic composition of claim 12, wherein said composition is in the form of a tablet.

21. The therapeutic composition of claim 12, further comprising a pharmaceutically acceptable excipient, a pharmaceutically acceptable carrier, or combinations thereof.

22. The therapeutic composition of claim 16, wherein the monoglyceride is glyceryl monooctanoate, glyceryl monodecanoate, glyceryl monolaurate, glyceryl monomyristate, glyceryl monostearate, glyceryl monopalmitate or glyceryl monooleate.

\* \* \* \* \*

UNITED STATES PATENT AND TRADEMARK OFFICE
CERTIFICATE OF CORRECTION

| | | |
|---|---|---|
| PATENT NO. | : 8,241,670 B2 | Page 1 of 1 |
| APPLICATION NO. | : 11/547568 | |
| DATED | : August 14, 2012 | |
| INVENTOR(S) | : Ben-Sasson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1214 days.

Signed and Sealed this
Eighth Day of January, 2013

David J. Kappos
*Director of the United States Patent and Trademark Office*